(12) United States Patent
Nomura et al.

(10) Patent No.: US 8,187,730 B2
(45) Date of Patent: May 29, 2012

(54) ACENAPHTHOQUINOXALINE DERIVATIVE, LIGHT-EMITTING ELEMENT, LIGHT-EMITTING DEVICE, AND ELECTRONIC DEVICE

(75) Inventors: Ryoji Nomura, Kanagawa (JP); Takako Takasu, Leuven (BE); Satoko Shitagaki, Kanagawa (JP); Tsunenori Suzuki, Kanagawa (JP); Satoshi Seo, Kanagawa (JP)

(73) Assignee: Semiconductor Energy Laboratory Co., Ltd. (JP)

( * ) Notice: Subject to any disclaimer, the term of this patent is extended or adjusted under 35 U.S.C. 154(b) by 523 days.

(21) Appl. No.: 12/408,342

(22) Filed: Mar. 20, 2009

(65) Prior Publication Data

US 2009/0243476 A1    Oct. 1, 2009

(30) Foreign Application Priority Data

Mar. 28, 2008    (JP) .................. 2008-087308

(51) Int. Cl.
*H01L 51/54*    (2006.01)

(52) U.S. Cl. ........ 428/690; 428/917; 313/504; 313/505; 313/506; 257/40; 257/E51.05; 544/234

(58) Field of Classification Search .................. 428/690, 428/917; 313/504, 505, 506; 257/40, E51.05; 544/234

See application file for complete search history.

(56) References Cited

FOREIGN PATENT DOCUMENTS

JP    2003-212875    *    7/2003

OTHER PUBLICATIONS

Tao, Y.T. et al, "Sharp Green Electroluminescence from 1H-Pyrazolo[3,4-b] Quinoline-Based Light-Emitting Diodes," Appl. Phys. Lett. (Applied Physics Letters) vol. 77, No. 11, Sep. 11, 2000, pp. 1575-1577.

* cited by examiner

*Primary Examiner* — Jennifer Chriss
*Assistant Examiner* — Gregory Clark
(74) *Attorney, Agent, or Firm* — Husch Blackwell LLP

(57) ABSTRACT

An acenaphthoquinoxaline derivative represented by a general formula (G1) is provided. The acenaphthoquinoxaline derivative represented by the general formula (G1) easily receives electrons and has an electron-transporting property. Therefore, the acenaphthoquinoxaline derivative can be suitably used for a light-emitting element.

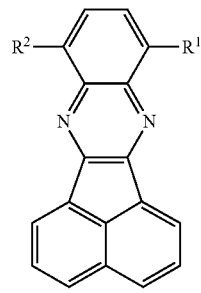

(G1)

16 Claims, 28 Drawing Sheets

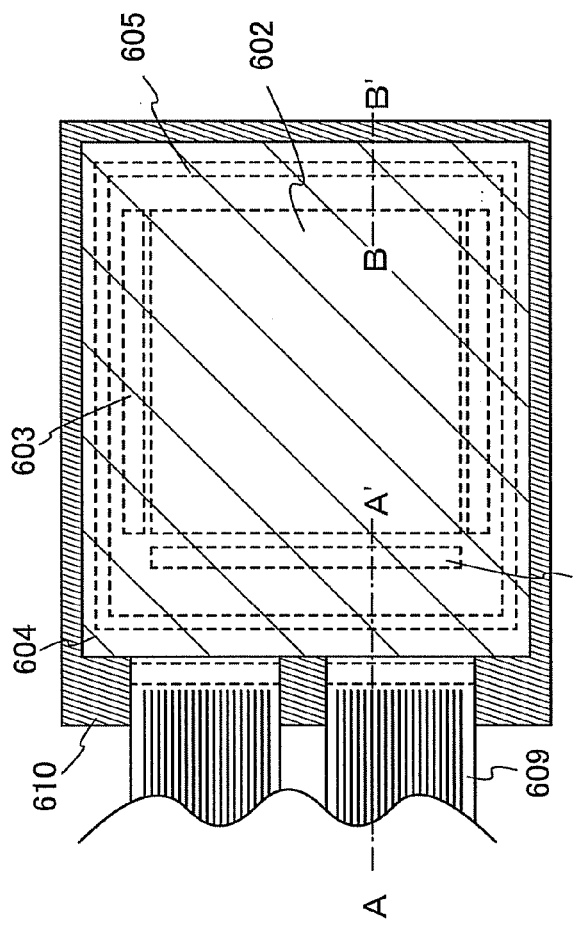
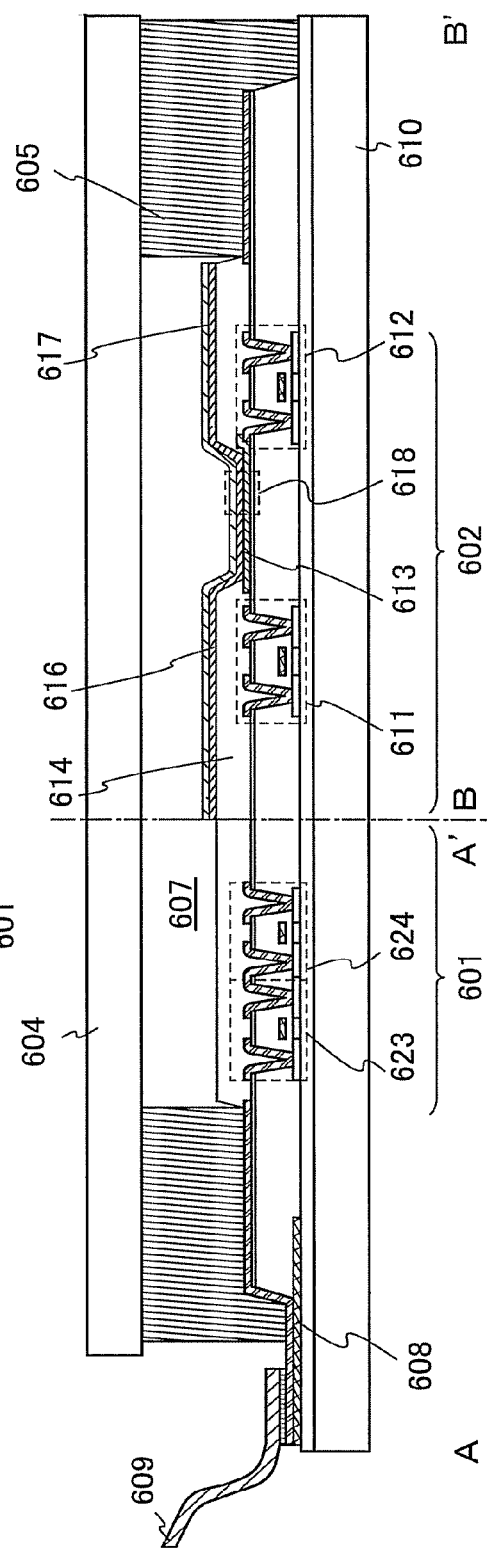
FIG. 6A
FIG. 6B

ACENAPHTHOQUINOXALINE DERIVATIVE, LIGHT-EMITTING ELEMENT, LIGHT-EMITTING DEVICE, AND ELECTRONIC DEVICE

BACKGROUND OF THE INVENTION

1. Field of the Invention

The present invention relates to a material applicable to a light-emitting element utilizing electroluminescence. Further, the present invention relates to a light-emitting element using the material and to a light-emitting device and an electronic device each using the light-emitting element.

2. Description of the Related Art

Organic compounds can take various structures compared with inorganic compounds, and it is possible to synthesize a material having a variety of functions by appropriate molecular design of an organic compound. Because of these types of advantages, attention has been focused on photo electronics and electronics in which functional organic compounds are used in recent years.

For example, as examples of electronic devices in which organic compounds are used as functional materials, there are solar cells, light-emitting elements, organic transistors, and the like. These devices use the electrical properties and optical properties of organic compounds. Among them, in particular, tremendous progress in light-emitting elements has been made.

It is said that the light emission mechanism of a light-emitting element is as follows: by application of a voltage between a pair of electrodes with a light-emitting layer interposed therebetween, electrons injected from a cathode and holes injected from an anode recombine in the luminescence center of the light-emitting layer to form excitons in molecules, and when the excitons in molecules relax to a ground state, energy is released to emit light. A singlet excited state and a triplet excited state are known as excited states, and it is thought that light emission can be obtained through either of the excited states.

In an attempt to improve the performance of such a light-emitting element, there are many problems depending on a material, and in order to solve these problems, improvement of an element structure, development of a material, and the like have been carried out.

For example, as an electron-transporting material for a light-emitting element, 2,2',2"-(1,3,5-benzenetriyl)-tris(1-phenyl-1H-benzimidazole) (abbreviation: TPBI) or the like is widely used (see Reference 1: Y. T. Tao and three others, *Applied Physics Letter*, Vol. 77, No. 11, p. 1575, 2000). However, development of a material with more excellent characteristics such as further higher mobility has been demanded. In particular, in view of commercialization, a reduction in power consumption is an important object, and development of a material and a light-emitting element with more excellent characteristics has been desired.

SUMMARY OF THE INVENTION

In view of the foregoing problems, according to the present invention, a novel acenaphthoquinoxaline derivative is provided.

Furthermore, according to the present invention, driving voltage of a light-emitting element is reduced.

Moreover, according to the present invention, power consumption of a light-emitting element, a light-emitting device, or an electronic device is reduced.

As a result of intense study, the present inventors have synthesized an acenaphthoquinoxaline derivative represented by a general formula (G1) and found that the acenaphthoquinoxaline derivative easily receives electrons and has an electron-transporting property.

Thus, an embodiment of the present invention is an acenaphthoquinoxaline derivative represented by the general formula (G1).

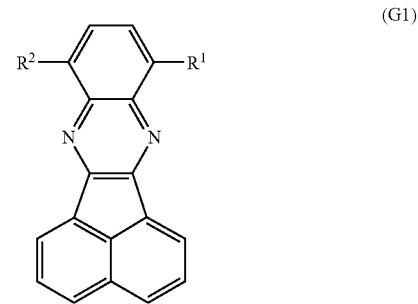

(G1)

In the formula, $R^1$ represents a substituted or unsubstituted aryl group having 6 to 13 carbon atoms, and $R^2$ represents a substituted or unsubstituted aryl group having 6 to 13 carbon atoms.

In the general formula (G1), $R^1$ is preferably a substituted or unsubstituted phenyl group for ease of synthesis. Further, $R^2$ is preferably a substituted or unsubstituted phenyl group.

In particular, because an acenaphthoquinoxaline derivative represented by a structural formula (101) where $R^1$ and $R^2$ are phenyl groups can be readily synthesized, the acenaphthoquinoxaline derivative is preferable.

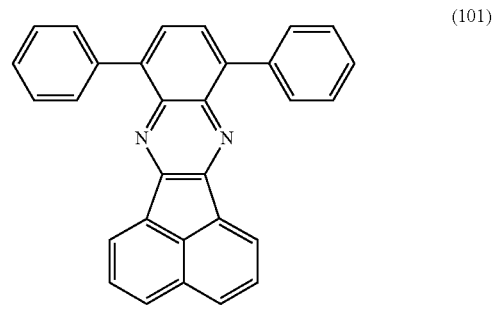

(101)

Further, the above acenaphthoquinoxaline derivative can be suitably used for a light-emitting element.

Thus, an embodiment of the present invention is a light-emitting element including the above acenaphthoquinoxaline derivative between a pair of electrodes.

In particular, since the above acenaphthoquinoxaline derivative easily receives electrons and has an electron-transporting property, the acenaphthoquinoxaline derivative is preferably used for an electron-transporting layer or an electron-injecting layer.

Thus, an embodiment of the present invention is a light-emitting element that includes a light-emitting layer and a layer including the above acenaphthoquinoxaline derivative between an anode and a cathode. The layer including the acenaphthoquinoxaline derivative is provided between the light-emitting layer and the cathode.

Further, because the above acenaphthoquinoxaline derivative has a lowest unoccupied molecular orbital level (LUMO level) which is low, the acenaphthoquinoxaline derivative can be used as an electron-trapping material.

Thus, an embodiment of the present invention is a light-emitting element that includes a light-emitting layer and a layer including the above acenaphthoquinoxaline derivative between an anode and a cathode. The layer including the acenaphthoquinoxaline derivative is provided between the light-emitting layer and the cathode and further includes an electron-transporting material. The amount of the electron-transporting material is larger than the amount of the acenaphthoquinoxaline derivative. The lowest unoccupied molecular orbital level (LUMO level) of the electron-transporting material is higher than the lowest unoccupied molecular orbital level (LUMO level) of the acenaphthoquinoxaline derivative.

Moreover, the present invention also includes a light-emitting device having the above light-emitting element.

Thus, an embodiment of the present invention is a light-emitting device having a light-emitting element including the above acenaphthoquinoxaline derivative and a control circuit configured to control light emission from the light-emitting element.

Note that the light-emitting device in this specification includes an image display device, a light-emitting device, and a light source (including a lighting apparatus). Further, the following are all included in a light-emitting device: a module in which a connector, for example, a flexible printed circuit (FPC), a tape automated bonding (TAB) tape, or a tape carrier package (TCP) is attached to a panel provided with a light-emitting element, a module provided with a printed wiring board at the end of a TAB tape or a TCP, and a module in which an integrated circuit (IC) is directly mounted to a light-emitting element by a chip on glass (COG) method.

Further, an electronic device using a light-emitting element of the present invention in a display portion is also included in the scope of the present invention. Accordingly, an embodiment of the present invention is an electronic device having a display portion, and the display portion includes the above light-emitting element and a control circuit configured to control light emission from the light-emitting element.

Since an acenaphthoquinoxaline derivative of the present invention easily receives electrons and has an electron-transporting property, the acenaphthoquinoxaline derivative can be suitably used for a light-emitting element.

Further, by using an acenaphthoquinoxaline derivative of the present invention for a light-emitting element driving voltage of the light-emitting element can be reduced. In addition, power consumption of the light-emitting element can be reduced.

Furthermore, by applying a light-emitting element of the present invention to a light-emitting device or an electronic device, power consumption of the light-emitting device or the electronic device can be reduced.

BRIEF DESCRIPTION OF THE DRAWINGS

FIGS. 6A and 6B illustrate a light-emitting device according to an embodiment of the present invention.

DETAILED DESCRIPTION OF THE INVENTION

Figure 1:
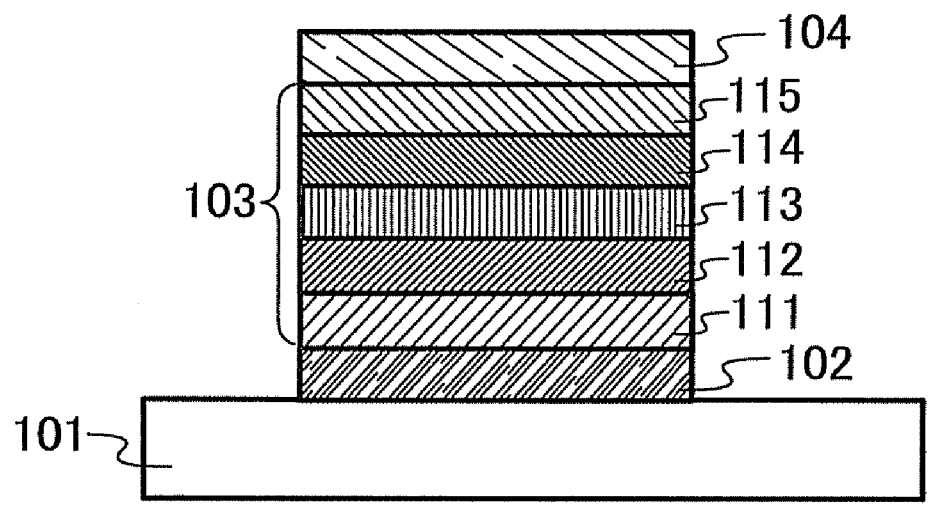
FIG. 1 illustrates a light-emitting element according to an embodiment of the present invention.

Hereinafter, embodiments of the present invention will be described in detail with reference to the accompanying drawings. Note that the present invention is not limited to the description below, and it is easily understood by those skilled in the art that a variety of changes and modifications can be made without departing from the spirit and scope of the present invention. Therefore, the present invention should not be interpreted as being limited to the content of the embodiments described below.

Embodiment 1

In Embodiment 1, an acenaphthoquinoxaline derivative of the present invention is described.

An acenaphthoquinoxaline derivative according to the present invention is the acenaphthoquinoxaline derivative represented by the general formula (G1).

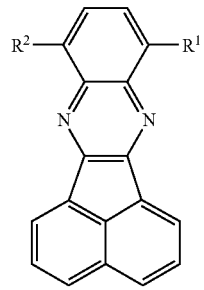

(G1)

In the formula, $R^1$ represents a substituted or unsubstituted aryl group having 6 to 13 carbon atoms, and $R^2$ represents a substituted or unsubstituted aryl group having 6 to 13 carbon atoms.

Note that the carbon atoms of the aryl group described in this specification refer to carbon atoms that form a ring of the main skeleton, and carbon atoms of a substituent bound thereto are not included therein. As examples of a substituent bonded to the aryl group, there are an alkyl group having 1 to 4 carbon atoms and an aryl group having 6 to 13 carbon atoms; specifically, there are a methyl group, an ethyl group, a propyl group, a butyl group, a phenyl group, a naphthyl group, a fluorenyl group, and the like. Further, the aryl group may have one or more substituents. If the aryl group has two substituents, the substituents may be bonded to each other to form a ring. For example, if the aryl group is a fluorenyl group, the carbon atom at the 9-position may have two phenyl groups, and the two phenyl groups may be bonded to each other to form a spiro ring structure.

As the substituted or unsubstituted aryl group having 6 to 13 carbon atoms of the acenaphthoquinoxaline derivative represented by the general formula (G1), aryl groups represented by structural formulae (11-1) to (11-16) are given, for example.

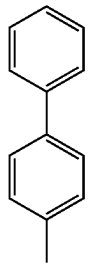

(11-1)

(11-2)

(11-3)

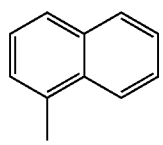

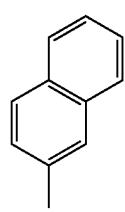

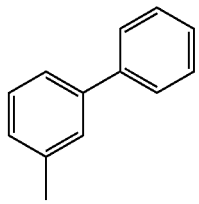

(11-4)

(11-5)

(11-6)

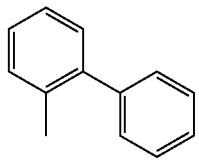

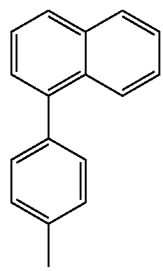

(11-7)

(11-8)

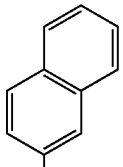

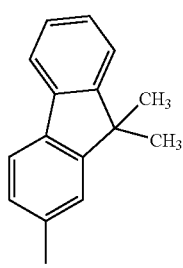

(11-9)

-continued (11-10)
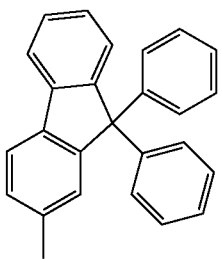

(11-11)
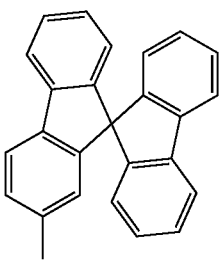

(11-12)
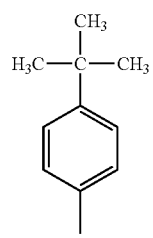

(11-13)
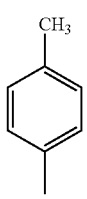

(11-14)
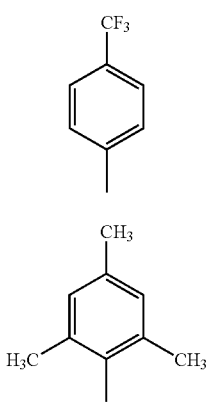

(11-15)
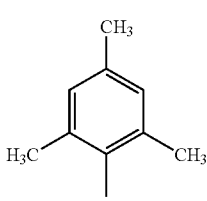

(11-16)
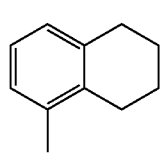

The acenaphthoquinoxaline derivative represented by the general formula (G1) easily receives electrons and tends to be reduced. Accordingly, the acenaphthoquinoxaline derivative can be suitably used for an electronic device such as a light-emitting element or an organic transistor.

As the acenaphthoquinoxaline derivative represented by the general formula (G1), acenaphthoquinoxaline derivatives represented by structural formulae (101) to (116) are given, for example. However, the present invention is not limited to these examples.

(101)
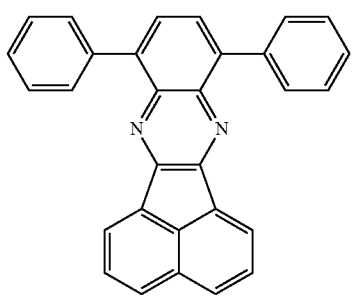

(102)
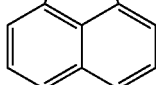

(103)
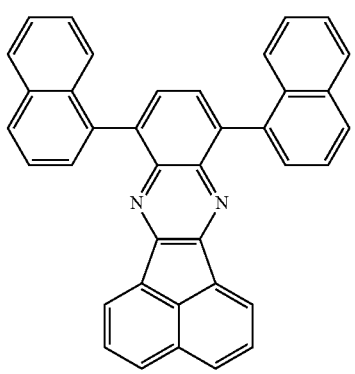

(104)
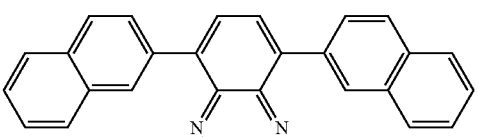

(105)
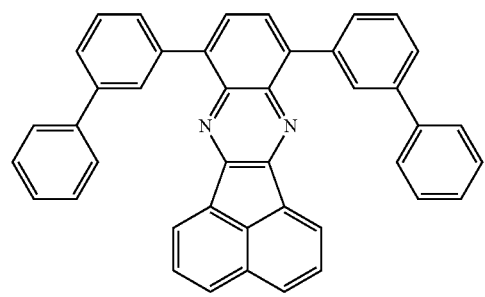
(106)
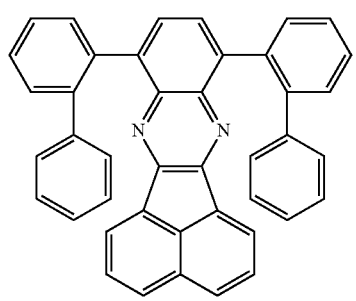
(107)
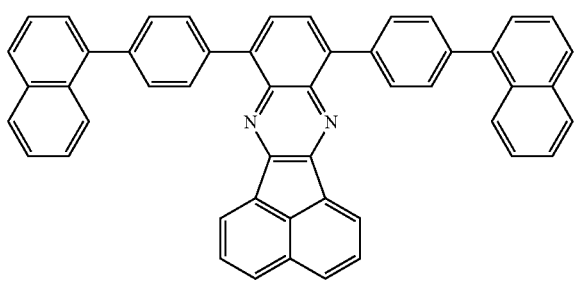
(108)
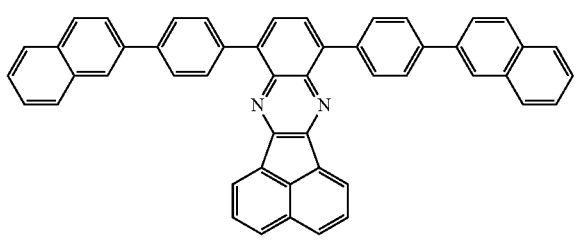
(109)
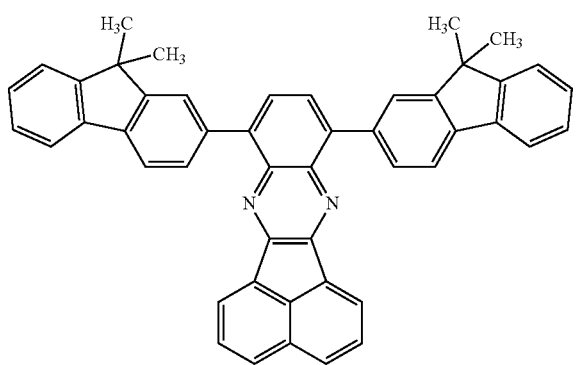
(110)
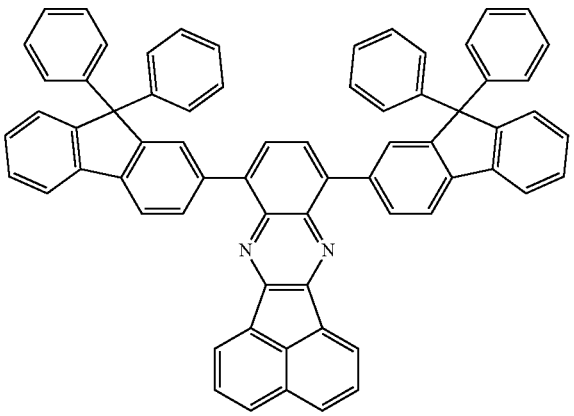
(111)
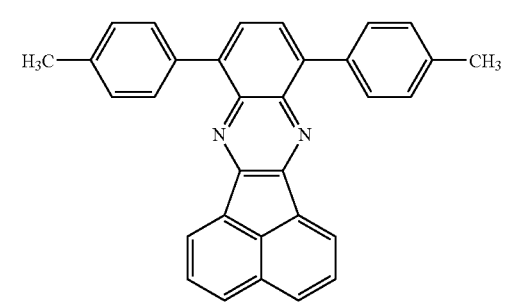
(112)
(113)
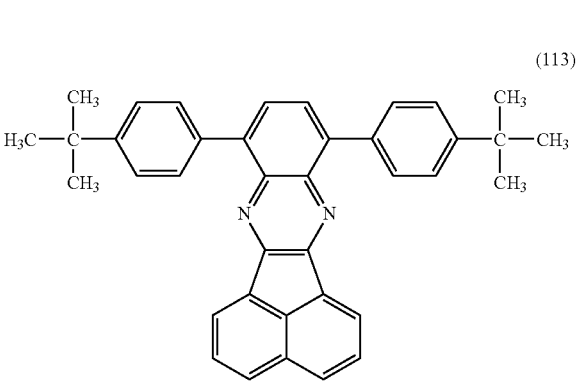

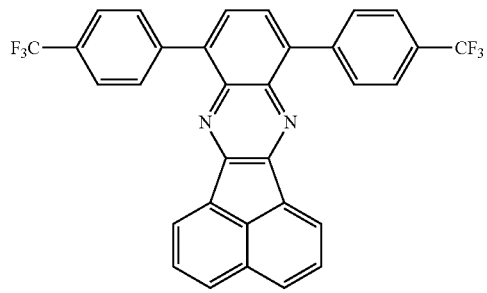
(114)

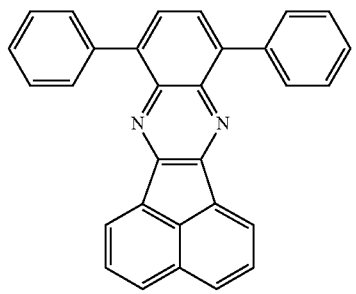
(101)

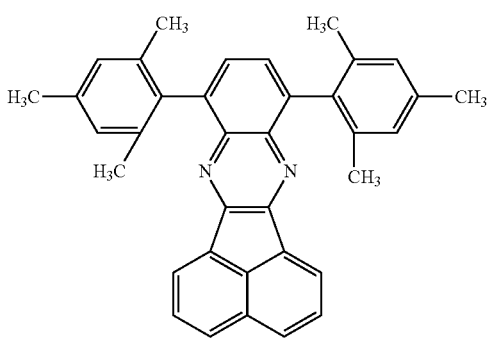
(115)

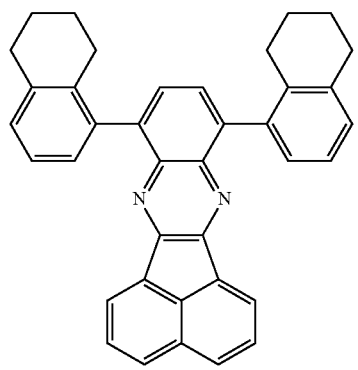
(116)

Preferably, $R^1$ and $R^2$ of the acenaphthoquinoxaline derivative represented by the general formula (G1) are the same substituents. With $R^1$ and $R^2$ which are the same substituents, the number of synthesis steps are reduced, whereby time and cost required for the synthesis can be reduced.

Further, in the acenaphthoquinoxaline derivative represented by the general formula (G1), $R^1$ is preferably a substituted or unsubstituted phenyl group for ease of synthesis. In addition, $R^2$ is preferably a substituted or unsubstituted phenyl group.

In particular, since the acenaphthoquinoxaline derivative represented by the general formula (G1) where $R^1$ and $R^2$ are phenyl group, i.e., the acenaphthoquinoxaline derivative represented by the structural formula (101) can be easily synthesized, the acenaphthoquinoxaline derivative is preferable.

A variety of reactions can be applied to a method of synthesizing the acenaphthoquinoxaline derivative described in Embodiment 1. For example, by synthesis reactions described below, the acenaphthoquinoxaline derivative described in Embodiment 1 can be synthesized. Note that the method of synthesizing the acenaphthoquinoxaline derivative described in Embodiment 1 is not limited to synthesis methods below.

⟨Synthesis Method of Acenaphthoquinoxaline Derivative Represented by General Formula (G1)⟩

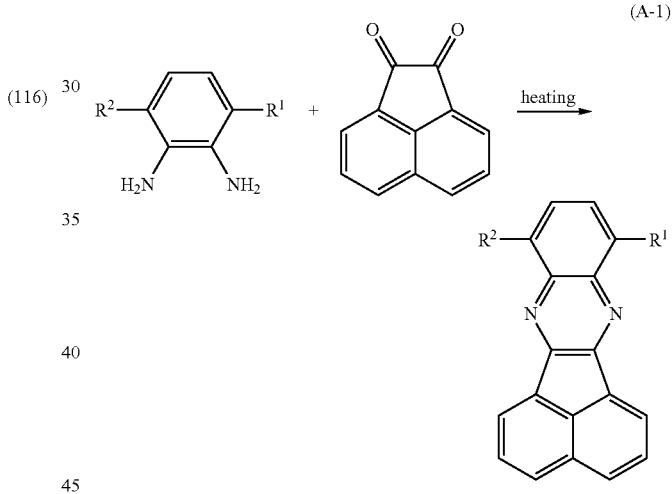
(A-1)

As illustrated in a synthesis scheme (A-1), a 3,6-diaryl 1,2-phenylenediamine derivative and acenaphthene-1,2-dione are heated in a solvent whereby an acenaphtho[1,2-b]quinoxaline derivative can be obtained. In the synthesis scheme, $R^1$ and $R^2$ represent aryl groups each having 6 to 13 carbon atoms that form a ring, and $R^1$ and $R^2$ may be the same or different from each other. Examples of a solvent that can be used in this reaction include alcohols such as ethanol, methanol, and butanol; aliphatic hydrocarbons such as hexane and cyclohexane; aromatic hydrocarbons such as benzene, toluene, and xylene; alkyl halides such as chloroform, dichloromethane, carbon tetrachloride, 1,2-dichloroethane, and 1,1,2,2-tetrachloromethane; and the like. However, solvents that can be used are not limited to these. Further, in an alcohol, the acenaphtho[1,2-b]quinoxaline derivative that is the object of the synthesis has low solubility; accordingly, in many cases, only the object is precipitated after reaction. The purification process in such a case can be performed simply by collecting the precipitated solid and recrystallizing the collected solid; thus, the process is remarkably simplified. Therefore, an alcohol is preferably used.

The acenaphthoquinoxaline derivative represented by the general formula (G1) easily receives electrons and tends to be reduced. Further, the acenaphthoquinoxaline derivative represented by the general formula (G1) has an electron-transporting property. Therefore, by using an acenaphthoquinoxaline derivative of the present invention for an electronic device such as a light-emitting element or an organic transistor, good electrical properties can be obtained.

Embodiment 2

In Embodiment 2, one embodiment of a light-emitting element using the acenaphthoquinoxaline derivative described in Embodiment 1 will be described with reference to FIG. 1 and FIG. 2.

A light-emitting element described in Embodiment 2 has a plurality of layers between a pair of electrodes. The plurality of layers are a stack of layers each including a substance having a high carrier-injecting property or a substance having a high carrier-transporting property such that a light-emitting zone is formed in a region away from the electrodes, i.e., such that carriers recombine in an area away from the electrodes.

In Embodiment 2, the light-emitting element includes a first electrode 102, a second electrode 104, and an EL layer 103 formed between the first electrode 102 and the second electrode 104. Note that in Embodiment 2, hereinafter, it is assumed that the first electrode 102 functions as an anode and the second electrode 104 functions as a cathode. In other words, in the description below, it is assumed that light emission is obtained when a voltage is applied to the first electrode 102 and the second electrode 104 so that the potential of the first electrode 102 is higher than that of the second electrode 104.

A substrate 100 is used as a support of the light-emitting element. For the substrate 100, glass, plastic, metal, or the like can be used, for example. Note that any other material may be used as long as it functions as a support of the light-emitting element. Note that when light emission from the light-emitting element is extracted outside through the substrate, a light-transmitting substrate is preferably used as the substrate 101.

Preferably, the first electrode 102 is formed using any of metals, alloys, or conductive compounds, a mixture thereof or the like having a high work function (specifically greater than or equal to 4.0 eV is preferable). For example, there are indium oxide-tin oxide (ITO), indium oxide-tin oxide containing silicon or silicon oxide, indium oxide-zinc oxide (IZO), indium oxide containing tungsten oxide and zinc oxide (IWZO), and the like. Films of such conductive metal oxide are normally formed by sputtering, but may also be formed by an inkjet method, a spin coating method, or the like by applying a sol-gel method or the like. For example, a film of indium oxide-zinc oxide (IZO) can be formed using a target in which 1 to 20 wt % of zinc oxide is added to indium oxide by a sputtering method. In addition, a film of indium oxide containing tungsten oxide and zinc oxide (IWZO) can be formed using a target in which 0.5 to 5 wt % tungsten oxide and 0.1 to 1 wt % zinc oxide are added to indium oxide by a sputtering method. Further, there are gold (Au), platinum (Pt), nickel (Ni), tungsten (W), chromium (Cr), molybdenum (Mo), iron (Fe), cobalt (Co), copper (Cu), palladium (Pd), titanium (Ti), nitride of a metal material (e.g., titanium nitride), and the like.

Further, when a layer including a composite material described later is used as a layer that is in contact with the first electrode 102, any of a variety of metals, alloys, electrically conductive compounds, or a mixture thereof can be used for the first electrode 102 regardless of the work functions. For example, aluminum (Al), silver (Ag), an alloy containing aluminum (e.g., AlSi), or the like can be used. Alternatively, it is possible to use any of elements belonging to Group 1 or 2 of the periodic table which have a low work function, i.e., alkali metals such as lithium (Li) and cesium (Cs); alkaline earth metals such as magnesium (Mg), calcium (Ca), and strontium (Sr); alloys containing any of these metals (e.g., MgAg and AlLi); rare earth metals such as europium (Eu) and ytterbium (Yb); alloys containing any of these metals; or the like. A film of an alkali metal, an alkaline earth metal, or an alloy containing any of these metals can be formed by a vacuum evaporation method. Alternatively, a film of an alloy containing an alkali metal or an alkaline earth metal can be formed by a sputtering method. Further, a film can be formed using silver paste or the like by an inkjet method or the like.

The EL layer 103 described in Embodiment 2 includes a hole-injecting layer 111, a hole-transporting layer 112, a light-emitting layer 113, an electron-transporting layer 114, and an electron-injecting layer 115. Note that it is acceptable as long as the EL layer 103 includes the acenaphthoquinoxaline derivative described in Embodiment 1 and there is no limitation on the stack structure of the other layers. That is, there is no limitation on the stack structure of the EL layer 103, and the EL layer 103 has a structure in which the acenaphthoquinoxaline derivative described in Embodiment 1 is used in combination with a layer including a substance having a high electron-transporting property, a substance having a high hole-transporting property, a substance having a high electron-injecting property, a substance having a high hole-injecting property, a bipolar substance (a substance having a high electron-transporting property and a high hole-transporting property), or the like, as appropriate. For example, the structure can be formed by combining a hole-injecting layer, a hole-transporting layer, a light-emitting layer, an electron-transporting layer, an electron-injecting layer, etc., as appropriate. Materials for the layers are specifically given below.

The hole-injecting layer 111 is a layer including a substance having a high hole-injecting property. As a substance having a high hole-injecting property, molybdenum oxide, vanadium oxide, ruthenium oxide, tungsten oxide, manganese oxide, or the like can be used. Besides, as examples of low molecular organic compounds, there are phthalocyanine-based compounds such as phthalocyanine (abbreviation: $H_2Pc$), copper(II) phthalocyanine (abbreviation: CuPc), and vanadyl(IV) phthalocyanine (VOPc), aromatic amine compounds such as 4,4',4"-tris(N,N-diphenylamino)triphenylamine (abbreviation: TDATA), 4,4',4"-tris[N-(3-methylphenyl)-N-phenylamino]triphenylamine (abbreviation: MTDATA), 4,4'-bis[N-(4-diphenylaminophenyl)-N-phenylamino]biphenyl (abbreviation: DPAB), 4,4'-bis(N-{4-[N'-(3-methylphenyl)-N'-phenylamino]phenyl}-N-phenylamino)biphenyl (abbreviation: DNTPD), 1,3,5-tris[N-(4-diphenylaminophenyl)-N-phenylamino]benzene (abbreviation: DPA3B), 3-[N-(9-phenylcarbazol-3-yl)-N-phenylamino]-9-phenylcarbazole (abbreviation: PCzPCA1), 3,6-bis[N-(9-phenylcarbazol-3-yl)-N-phenylamino]-9-phenylcarbazole (abbreviation: PCzPCA2), and 3-[N-(1-naphthyl)-N-(9-phenylcarbazol-3-yl)amino]-9-phenylcarbazole (abbreviation: PCzPCN1), and the like.

Alternatively, the hole-injecting layer 111 can be formed using a composite material in which an acceptor substance is included in a substance having a high hole-transporting property. Note that, by using a material in which an acceptor substance is included in a substance having a high hole-transporting property, a material used for forming the electrode may be selected regardless of the work function. In other words, besides a material with a high work function, a material with a low work function may also be used for the first electrode 102. Such composite materials can be formed by co-evaporation of a substance having a high hole-transporting property and an acceptor substance.

Note that in this specification, the term "composite" refers not only to a state in which two kinds of materials are simply mixed, but also to a state in which charges can be given and received between materials by mixture of a plurality of materials.

As an organic compound used for the composite material, any of a variety of compounds such as aromatic amine compounds, carbazole derivatives, aromatic hydrocarbons, or high molecular compounds (oligomers, dendrimers, polymers, etc.) can be used. Note that an organic compound used for the composite material preferably has a high hole-transporting property. Specifically, a substance having a hole mobility of $10^{-6}$ cm$^2$/Vs or more is preferably used. Further, any other substance may be used as long as it is a substance in which the hole-transporting property is higher than the electron-transporting property. Organic compounds that can be used for the composite material are specifically given below.

Examples of organic compounds that can be used for the composite material are as follows: aromatic amine compounds such as MTDATA, TDATA, DPAB, DNTPD, DPA3B, PCzPCA1, PCzPCA2, PCzPCN1, 4,4'-bis[N-(1-naphthyl)-N-phenylamino]biphenyl (abbreviation: NPB or α-NPD), and N,N'-bis(3-methylphenyl)-N,N'-diphenyl-[1,1'-biphenyl]-4,4'-diamine (abbreviation: TPD); carbazole derivatives such as 4,4'-di(N-carbazolyl)biphenyl (abbreviation: CBP), 1,3,5-tris[4-(N-carbazolyl)phenyl]benzene (abbreviation: TCPB), 9-[4-(10-phenyl-9-anthryl)phenyl]-9H-carbazole (abbreviation: CzPA), and 1,4-bis[4-(N-carbazolyl)phenyl]-2,3,5,6-tetraphenylbenzene; and aromatic hydrocarbon compounds such as 2-tert-butyl-9,10-di(2-naphthyl)anthracene (abbreviation: t-BuDNA), 2-tert-butyl-9,10-di(1-naphthyl)anthracene, 9,10-bis(3,5-diphenylphenyl)anthracene (abbreviation: DPPA), 2-tert-butyl-9,10-bis(4-phenylphenyl)anthracene (abbreviation: t-BuDBA), 9,10-di(2-naphthyl)anthracene (abbreviation: DNA), 9,10-diphenylanthracene (abbreviation: DPAnth), 2-tert-butylanthracene (abbreviation: t-BuAnth), 9,10-bis(4-methyl-1-naphthyl)anthracene (abbreviation: DMNA), 9,10-bis[2-(1-naphthyl)phenyl]-2-tert-butyl-anthracene, 9,10-bis[2-(1-naphthyl)phenyl]anthracene, 2,3,6,7-tetramethyl-9,10-di(1-naphthyl)anthracene, 2,3,6,7-tetramethyl-9,10-di(2-naphthyl)anthracene, 9,9'-bianthryl, 10,10'-diphenyl-9,9'-bianthryl, 10,10'-bis(2-phenylphenyl)-9,9'-bianthryl, 10,10'-bis[(2,3,4,5,6-pentaphenyl)phenyl]-9,9'-bianthryl, anthracene, tetracene, rubrene, perylene, 2,5,8,11-tetra(tert-butyl)perylene, pentacene, coronene, 4,4'-bis(2,2-diphenylvinyl)biphenyl (abbreviation: DPVBi), and 9,10-bis[4-(2,2-diphenylvinyl)phenyl]anthracene (abbreviation: DPVPA).

Further, examples of the acceptor substance are as follows: organic compounds such as 7,7,8,8-tetracyano-2,3,5,6-tetrafluoroquinodimethane (abbreviation: F$_4$-TCNQ) and chloranil, and transition metal oxides. Furthermore, other examples are oxides of metals belonging to Group 4 to Group 8 of the periodic table. Specifically, vanadium oxide, niobium oxide, tantalum oxide, chromium oxide, molybdenum oxide, tungsten oxide, manganese oxide, and rhenium oxide are preferable because of their high electron-accepting properties. Among these, molybdenum oxide is especially preferable because it is stable in air and its hygroscopic property is low so that it can be easily handled.

Alternatively, for the hole-injecting layer 111, any of high molecular compounds (oligomers, dendrimers, polymers, etc.) can be used. Examples of high molecular compounds include poly(N-vinylcarbazole) (abbreviation: PVK), poly (4-vinyltriphenylamine) (abbreviation: PVTPA), poly[N-(4-{N'-[4-(4-diphenylamino)phenyl]phenyl-N'-phenylamino}phenyl)methacrylamide] (abbreviation: PTPDMA), and poly[N',N'-bis(4-butylphenyl)-N,N'-bis (phenyl)benzidine (abbreviation: Poly-TPD). Alternatively, a high molecular compound to which acid is added, such as poly(3,4-ethylenedioxythiophene)/poly(styrenesulfonic acid) (PEDOT/PSS) or polyaniline/poly(styrenesulfonic acid) (PAni/PSS), can be used.

Alternatively, for the hole-injecting layer 111, a composite material formed using any of the above-mentioned high molecular compounds such as PVK, PVTPA, PTPDMA, or Poly-TPD and any of the above-mentioned acceptor substances may be used.

The hole-transporting layer 112 is a layer including a substance having a high hole-transporting property. As a substance having a high hole-transporting property, a low molecular organic compound can be used, and examples thereof include aromatic amine compounds such as NPB (or α-NPD), TPD, 4,4'-bis[N-(9,9-dimethylfluoren-2-yl)-N-phenylamino]biphenyl (abbreviation: DFLDPBi), and 4,4'-bis[N-(spiro-9,9'-bifluoren-2-yl)-N-phenylamino]biphenyl (abbreviation: BSPB). The substances mentioned here are mainly substances having a hole mobility of $10^{-6}$ cm$^2$/Vs or more. However, any other substance may also be used as long as it is a substance in which the hole-transporting property is higher than the electron-transporting property. Note that the hole-transporting layer is not limited to a single layer and may be a stack of two or more layers including any of the above-mentioned substances.

Alternatively, for the hole-transporting layer 112, a composite material in which an acceptor substance is included in the above-mentioned substance having a high hole-transporting property may be used.

Alternatively, for the hole-transporting layer 112, a high molecular compound such as PVK, PVTPA, PTPDMA, or Poly-TPD can be used.

The light-emitting layer 113 is a layer including a substance having a high light-emitting property, and can be formed using any of a variety of materials. As a substance having a high light-emitting property, for example, a fluorescent compound which emits fluorescence or a phosphorescent compound which emits phosphorescence can be used.

Examples of phosphorescent compounds that can be used for the light-emitting layer are given below. Examples of materials for blue light emission are as follows: bis[2-(4',6'-difluorophenyl)pyridinato-N,C$^{2'}$]iridium(III) tetrakis(1-pyrazolyl)borate (abbreviation: FIr6), bis[2-(4',6'-difluorophenyl)pyridinato-N,C$^{2'}$]iridium(III) picolinate (abbreviation: FIrpic), bis[2-(3',5'bistrifluoromethylphenyl)pyridinato-N,C$^{2'}$]iridium(III) picolinate (abbreviation: Ir(CF$_3$ppy)$_2$(pic)), bis[2-(4',6'-difluorophenyl)pyridinato-N,C$^{2'}$]iridium(III) acetylacetonate (abbreviation: FIracac), and the like. Further, examples of materials for green light emission are as follows: tris(2-phenylpyridinato-N,C$^{2'}$)iridium(III) (abbreviation: Ir(ppy)$_3$), bis(2-phenylpyridinato-N,C$^{2'}$)iridium(III) acetylacetonate (abbreviation. Ir(ppy)$_2$(acac)), bis(1,2-diphenyl-1H-benzimidazolato)iridium(III) acetylacetonate (abbreviation: Ir(pbi)$_2$(acac)), bis(benzo[h]quinolinato)iridium(III) acetylacetonate (abbreviation: Ir(bzq)$_2$(acac)), and the like. Further, examples of materials for yellow light emission are as follows: bis(2,4-diphenyl-1,3-oxazolato-N,C$^{2'}$)iridium (III) acetylacetonate (abbreviation: Ir(dpo)$_2$(acac)), bis[2-(4'-perfluorophenylphenyl)pyridinato]iridium(III) acetylacetonate (abbreviation: Ir(p-PF-ph)$_2$(acac)), bis(2- phenylbenzothiazolato-N,C$^{2'}$)iridium(III) acetylacetonate (abbreviation: Ir(bt)$_2$(acac)), and the like. Further, examples of materials for orange light emission are as follows: tris(2-phenylquinolinato-N,C$^{2'}$)iridium(III) (abbreviation: Ir(pq)$_3$), bis(2-phenylquinolinato-N,C$^{2'}$)iridium(III) acetylacetonate (abbreviation: Ir(pq)$_2$(acac)), and the like. Further, examples of materials for red light emission are organometallic complexes such as bis[2-(2'-benzo[4,5-a]thienyl)pyridinato-N,C$^{3'}$]iridium(III) acetylacetonate (abbreviation: Ir(btp)$_2$(acac)), bis(1-phenylisoquinolinato-N,C$^{2'}$)iridium(III) acetylacetonate (abbreviation: Ir(piq)$_2$(acac)), (acetylacetonato)bis[2,3-bis(4-fluorophenyl)quinoxalinato]iridium(III) (abbreviation: Ir(Fdpq)$_2$(acac)), and 2,3,7,8,12,13,17,18-octaethyl-21H,23H-porphyrin platinum(II) (abbreviation: PtOEP). In addition, since a rare earth metal complex such as tris(acetylacetonato)(monophenanthroline)terbium(III) (abbreviation: Tb(acac)$_3$(Phen)), tris(1,3-diphenyl-1,3-propanedionato)(monophenanthroline)europium(III) (abbreviation: Eu(DBM)$_3$(Phen)), or tris[1-(2-thenoyl)-3,3,3-trifluoroacetonato](monophenanthroline)europium(III) (abbreviation: Eu(TTA)$_3$(Phen)) exhibits light emission from a rare earth metal ion (hole transition between different multiplets), such a rare earth metal complex can be used as a phosphorescent compound.

Examples of fluorescent compounds that can be used for the light-emitting layer are given below. Examples of materials for blue light emission are as follows: N,N'-bis[4-(H-carbazol-9-yl)phenyl]-N,N'-diphenylstilbene-4,4'-diamine (abbreviation: YGA2S), 4-(9H-carbazol-9-yl)-4'-(10-phenyl-9-anthryl)triphenylamine (abbreviation: YGAPA), and the like. Further, examples of materials for green light emission are as follows: N-(9,10-diphenyl-2-anthryl)-N,9-diphenyl-9H-carbazol-3-amine (abbreviation: 2PCAPA), N-[9,10-bis(1,1'-biphenyl-2-yl)-2-anthryl]-N,9-diphenyl-9H-carbazol-3-amine (abbreviation: 2PCABPhA), N-(9,10-diphenyl-2-anthryl)-N,N',N'-triphenyl-9,4-phenylenediamine (abbreviation: 2DPAPA), N-[9,10-bis(1,1'-biphenyl-2-yl)-2-anthryl]-N,N',N'-triphenyl-1,4-phenylenediamine (abbreviation: 2DPABPhA), 9,10-bis(1,1'-biphenyl-2-yl)-N-[4-(9H-carbazol-9-yl)phenyl]-N-phenylanthracen-2-amine (abbreviation: 2YGABPhA), N,N,9-triphenylanthracen-9-amine (abbreviation: DPhAPhA), and the like. Further, examples of materials for yellow light emission are as follows: rubrene, 5,12-bis(1,1'-biphenyl-4-yl)-6,11-diphenyltetracene (abbreviation: BPT), and the like. Further, examples of materials for red light emission are as follows: N,N,N',N'-tetrakis(4-methylphenyl)tetracene-5,11-diamine (abbreviation: p-mPhTD), 7,13-diphenyl-N,N,N',N'-tetrakis(4-methylphenyl)acenaphtho[1,2-a]fluoranthene-3,10-diamine (abbreviation: p-mPhAFD), 2-(2-{2-[4-(dimethylamino)phenyl]ethenyl}-6-methyl-4H-pyran-4-ylidene)propanedinitrile (abbreviation: DCM1), 2-{2-methyl-6-[2-(2,3,6,7-tetrahydro-1H,5H-benzo[ij]quinolizin-9-yl)ethenyl]-4H-pyran-4-ylidene}propanedinitrile (abbreviation: DCM2), and the like.

Note that the light-emitting layer may have a structure in which the above substance having a high light-emitting property (a guest material) is dispersed into another substance (a host material). As a substance in which a substance having a high light-emitting property is dispersed, a variety of kinds of substances can be used, and it is preferable to use a substance that has a lowest unoccupied molecular orbital (LUMO) level higher than that of a substance having a high light-emitting property and has a highest occupied molecular orbital (HOMO) level lower than that of the substance having a high light-emitting property.

Specific examples of a substance into which the substance having a light-emitting property is dispersed include metal complexes such as tris(8-quinolinolato)aluminum(III) (abbreviation: Alq), tris(4-methyl-8-quinolinolato)aluminum (III) (abbreviation: Almq$_3$), bis(10-hydroxybenzo[h]quinolinato)beryllium(II) (abbreviation: BeBq$_2$), bis(2-methyl-8-quinolinolato)(4-phenylphenolato)aluminum(III) (abbreviation: BAlq), bis(8-quinolinolato)zinc(II) (abbreviation: Znq), bis[2-(2-benzoxazolyl)phenolato]zinc(II) (abbreviation: ZnPBO), and bis[2-(2-benzothiazolyl)phenolato] zinc(II) (abbreviation: ZnBTZ); heterocyclic compounds such as 2-(4-biphenylyl)-5-(4-tert-butylphenyl)-1,3,4-oxadiazole (abbreviation: PBD), 1,3-bis[5-(p-tert-butylphenyl)-1,3,4-oxadiazol-2-yl]benzene (abbreviation: OXD-7), 3-(4-biphenylyl)-4-phenyl-5-(4-tert-butylphenyl)-1,2,4-triazole (abbreviation: TAZ), 2,2',2''-(1,3,5-benzenetriyl)tris(1-phenyl-1H-benzimidazole) (abbreviation: TPBI), bathophenanthroline (abbreviation: BPhen), and bathocuproine (abbreviation: BCP); condensed aromatic compounds such as 9-[4-(10-phenyl-9-anthryl)phenyl]-9H-carbazole (abbreviation: CzPA), 3,6-diphenyl-9-[4-(10-phenyl-9-anthryl)phenyl]-9H-carbazole (abbreviation: DPCzPA), 9,10-bis(3,5-diphenylphenyl)anthracene (abbreviation: DPPA), 9,10-di(2-naphthyl)anthracene (abbreviation: DNA), 2-tert-butyl-9,10-di(2-naphthyl)anthracene (abbreviation: t-BuDNA), 9,9'-bianthryl (abbreviation: BANT), 9,9'-(stilbene-3,3'-diyl) diphenanthrene (abbreviation: DPNS), 9,9'-(stilbene-4,4'-diyl)diphenanthrene (abbreviation: DPNS2), 3,3',3''-(benzene-1,3,5-triyl)tripyrene (abbreviation: TPB3), 9,10-diphenylanthracene (abbreviation: DPAnth), and 6,12-dimethoxy-5,11-diphenylchrysene; aromatic amine compounds such as N,N-diphenyl-9-[4-(10-phenyl-9-antryl) phenyl]-9H-carbazol-3-amine (abbreviation: CzAlPA), 4-(10-phenyl-9-anthryl)triphenylamine (abbreviation: DPhPA), N,9-diphenyl-N-[4-(10-phenyl-9-anthryl)phenyl]-9H-carbazol-3-amine (abbreviation: PCAPA), N,9-diphenyl-N-{4-[4-(10-phenyl-9-anthryl)phenyl]phenyl}-9H-cabazol-3-amine (abbreviation: PCAPBA), N-(9,10-diphenyl-2-anthryl)-N,9-diphenyl-9H-carbazol-3-amine (abbreviation: 2PCAPA), NPB (or α-NPD), TPD, DFLDPBi, and BSPB; and the like.

Further, as a substance into which the substance having a light-emitting property is dispersed, a plurality of kinds of substances can be used. For example, in order to suppress crystallization, a substance for suppressing crystallization, such as rubrene, may be further added. Furthermore, in order to efficiently transfer energy to the substance having a light-emitting property, NPB, Alq or the like may be further added.

With a structure in which a substance having a high light-emitting property is dispersed into another substance, crystallization of the light-emitting layer 113 can be suppressed. Further, concentration quenching due to high concentration of the substance having a high light-emitting property can be suppressed.

Note that for the light-emitting layer 113, a high molecular compound can be used. Specifically, examples of materials for blue light emission are as follows: poly(9,9-dioctylfluorene-2,7-diyl) (abbreviation. POF), poly[(9,9-dioctylfluorene-2,7-diyl)-co-(2,5-dimethoxybenzene-1,4-diyl)] (abbreviation: PF-DMOP), poly{(9,9-dioctylfluorene-2,7-diyl)-co-[N,N'-di-(p-butylphenyl)-1,4-diaminobenzene]} (abbreviation: TAB-PFH), and the like. Further, examples of materials for green light emission are as follows: polyp-phenylenevinylene) (abbreviation: PPV), poly[(9,9-dihexylfluorene-2,7-diyl)-alt-co-(benzo[2,1,3]thiadiazole-4,7-diyl)] (abbreviation: PFBT), poly[(9,9-dioctyl-2,7-divinylenefluorenylene)-alt-co-(2-methoxy-5-(2-ethylhexyloxy)-1,4-phenylene)], and the like. Further, examples of materials for orange to red light emission are as follows: poly[2-methoxy-5-(2'-ethylhexoxy)-1,4-phenylenevinylene] (abbreviation: MEH-PPV), poly(3-butylthiophene-2,5-diyl) (abbreviation: R4-PAT), poly{[9,9-dihexyl-2,7-bis(1-cyanovinylene)fluorenylene]-alt-co-[2,5-bis(N,N'-diphenyl amino)-1,4-phenylene]}, poly{[2-methoxy-5-(2-ethylhexyloxy)-1,4-bis(1-cyanovinylenephenylene)]-alt-co-[2,5-bis(N,N'-diphenylamino)-1,4-phenylene]}(abbreviation: CN-PPV-DPD), and the like.

Note that since the acenaphthoquinoxaline derivative described in Embodiment 1 exhibits a light-emitting property, the acenaphthoquinoxaline derivative can be used for a light-emitting layer as a substance having a high light-emitting property. By using the acenaphthoquinoxaline derivative described in Embodiment 1 as a substance having a high light-emitting property, a blue to green light-emitting element can be obtained.

Further, the acenaphthoquinoxaline derivative described in Embodiment 1 can be used as a substance (a host material) into which a substance having a high light-emitting property is dispersed. When the acenaphthoquinoxaline derivative described in Embodiment 1 is used as a host material, as a guest material, rubrene, 2-(2-{2-[4-(dimethylamino)phenyl]ethenyl}-6-methyl-4H-pyran-4-ylidene)propanedinitrile (abbreviation: DCM1), 2-{2-methyl-6-[2-(2,3,6,7-tetrahydro-1H,5H-benzo[ij]quinolizin-9-yl)ethenyl]-4H-pyran-4-ylidene}propanedinitrile (abbreviation: DCM2), or the like can be used.

The electron-transporting layer 114 is a layer including a high electron-transporting property. Since the acenaphthoquinoxaline derivative described in Embodiment 1 has an electron-transporting property, the acenaphthoquinoxaline derivative can be suitably used for the electron-transporting layer 114. Note that the electron-transporting layer is not limited to a single layer, and may be a stack of two or more layers.

When the electron-transporting layer is a stack of two or more layers, a low molecular compound can be used as another substance having a high electron-transporting property. For example, there are metal complexes such as tris(8-quinolinolato)aluminum(III) (abbreviation: Alq), tris(4-methyl-8-quinolinolato)aluminum(III) (abbreviation: Almq$_3$), bis(10-hydroxybenzo[h]quinolinato)beryllium(II) (abbreviation: BeBq$_2$), bis(2-methyl-8-quinolinolato)(4-phenylphenolato)aluminum(III) (abbreviation: BAlq), bis(8-quinolinolato)zinc(II) (abbreviation: Znq), bis[2-(2-benzoxazolyl)phenolato]zinc(II) (abbreviation: ZnPBO), and bis[2-(2-benzothiazolyl)phenolato]zinc(II) (abbreviation: ZnBTZ). Furthermore, besides the metal complexes, there are heterocyclic compounds such as 2-(4-biphenylyl)-5-(4-tert-butylphenyl)-1,3,4-oxadiazole (abbreviation: PBD), 1,3-bis[5-(p-tert-butylphenyl)-1,3,4-oxadiazol-2-yl]benzene (abbreviation: OXD-7), 3-(4-biphenylyl)-4-phenyl-5-(4-tert-butylphenyl)-1,2,4-triazole (abbreviation: TAZ01), bathophenanthroline (abbreviation: BPhen), and bathocuproine (abbreviation: BCP). The substances mentioned here are mainly substances having an electron mobility of $10^{-6}$ cm$^2$/Vs or more. Note that any other substance may also be used as long as it is a substance in which the electron-transporting property is higher than the hole-transporting property. Further, the electron-transporting layer is not limited to a single layer and may be a stack of two or more layers including any of the above-mentioned substances.

When the electron-transporting layer is a stack of two or more layers, a high molecular compound can be used as another substance having a high electron-transporting property. For example, poly[(9,9-dihexylfluorene-2,7-diyl)-co-(pyridine-3,5-diyl)] (abbreviation: PF-Py), poly[(9,9-dioctylfluorene-2,7-diyl)-co-(2,2'-bipyridine-6,6'-diyl)] (abbreviation: PF-BPy), or the like can be used.

The electron-injecting layer 115 is a layer including a substance having a high electron-injecting property. As the substance having a high electron-injecting property, any of alkali metals, alkaline earth metals, or compounds thereof, such as lithium fluoride (LiF), cesium fluoride (CsF), and calcium fluoride (CaF$_2$) can be used. Further, a layer including a material having an electron-transporting property which contains an alkali metal, an alkaline earth metal, or a compound thereof, such as a layer including Alq which contains magnesium (Mg), can be used. Note that by using a layer including a material having an electron-transporting property which contains an alkali metal or an alkaline earth metal as the electron-injecting layer, injection of electrons from the second electrode 104 is performed efficiently, which is preferable.

Note that since the acenaphthoquinoxaline derivative described in Embodiment 1 easily receives electrons and has an electron-transporting property, the acenaphthoquinoxaline derivative can be used for an electron-injecting layer. When the acenaphthoquinoxaline derivative described in Embodiment 1 is used for an electron-injecting layer, the electron-injecting layer preferably includes the acenaphthoquinoxaline derivative described in Embodiment 1 and any of an alkali metal, an alkaline earth metal, or a compound thereof.

As a substance for forming the second electrode 104, a metal, an alloy, an electrically conductive compound, a mixture thereof, or the like with a low work function (specifically, a work function of 3.8 eV or lower is preferable) can be used. As specific examples of such cathode materials, there are elements belonging to Group 1 or Group 2 of the periodic table, i.e., alkali metals such as lithium (Li) and cesium (Cs); alkaline earth metals such as magnesium (Mg), calcium (Ca), and strontium (Sr); alloys containing any of these metals (e.g., MgAg and AlLi); rare earth metals such as europium (Eu) and ytterbium (Yb); alloys containing any of these metals; and the like. A film of an alkali metal, an alkaline earth metal, or an alloy containing any of these metals can be formed by a vacuum evaporation method. Alternatively, a film of an alloy containing an alkali metal or an alkaline earth metal can be formed by a sputtering method. Further, a film can be formed using silver paste or the like by an inkjet method or the like.

Further, by providing the electron-injecting layer 115 which is a layer having the function of promoting injection of electrons between the second electrode 104 and the electron-transporting layer 114, the second electrode 104 can be formed using any of a variety of conductive materials such as Al, Ag, ITO, or indium oxide-tin oxide containing silicon or silicon oxide, regardless of the work functions. Films of these conductive materials can be formed by a sputtering method, an inkjet method, a spin coating method, or the like.

Further, any of a variety of methods can be employed for forming the EL layer regardless of whether the method is a dry process or a wet process. For example, a vacuum evaporation method, an inkjet method, a spin coating method, or the like may be used. Further, a different formation method may be used for each electrode or each layer.

For example, the EL layer may be formed using a high molecular compound selected from the above-described materials by a wet method. Alternatively, the EL layer can be formed using a low molecular organic compound by a wet method. Further alternatively, the EL layer may be formed using a low molecular organic compound by a dry method such as vacuum evaporation.

In addition, the electrode may be formed by a wet method using a sol-gel method, or by a wet method using paste of a metal material. Alternatively, the electrode may be formed by a dry method such as a sputtering method or a vacuum evaporation method.

For example, when the light-emitting element described in Embodiment 2 is applied to a display device and the display device is fabricated using a large substrate, the light-emitting layer is preferably formed by a wet method. By forming light-emitting layers by an inkjet method, the light-emitting layers are easy to form in different colors even when a large substrate is used.

In the light-emitting element having the structure as described above, by application of a voltage, a current flows between the first electrode 102 and the second electrode 104, and holes and electrons recombine in the EL layer 103, whereby light is emitted.

The emitted light is extracted out through one or both of the first electrode 102 and the second electrode 104. Therefore, one or both of the first electrode 102 and the second electrode 104 is/are an electrode having a light transmitting property. For example, when only the first electrode 102 has a light transmitting property, the emitted light is extracted from a substrate side through the first electrode 102. Alternatively, when only the second electrode 104 has a light transmitting property, the emitted light is extracted from the side opposite to the substrate through the second electrode 104. When each of the first electrode 102 and the second electrode 104 has a light-transmitting property, the emitted light is extracted from both the substrate side and the side opposite to the substrate side through the first electrode 102 and the second electrode 104.

Note that the structure of layers provided between the first electrode 102 and the second electrode 104 are not limited to the above structure. Any structure instead of the above structure can be employed as long as the light-emitting zone for recombination of electrons and holes is positioned away from the first electrode 102 and the second electrode 104 so as to prevent quenching due to the proximity of the light-emitting zone and a metal, and the acenaphthoquinoxaline derivative described in Embodiment 1 is included in the structure.

That is, there is no limitation on the stack structure of the layers. The acenaphthoquinoxaline derivative described in Embodiment 1 is used in combination with a layer including a substance having a high electron-transporting property, a substance having a high hole-transporting property, a substance having a high electron-injecting property, a substance having a high hole-injecting property, or a substance having a bipolar property (a substance having a high electron-transporting property and a hole-transporting property), as appropriate.

Figure 2:
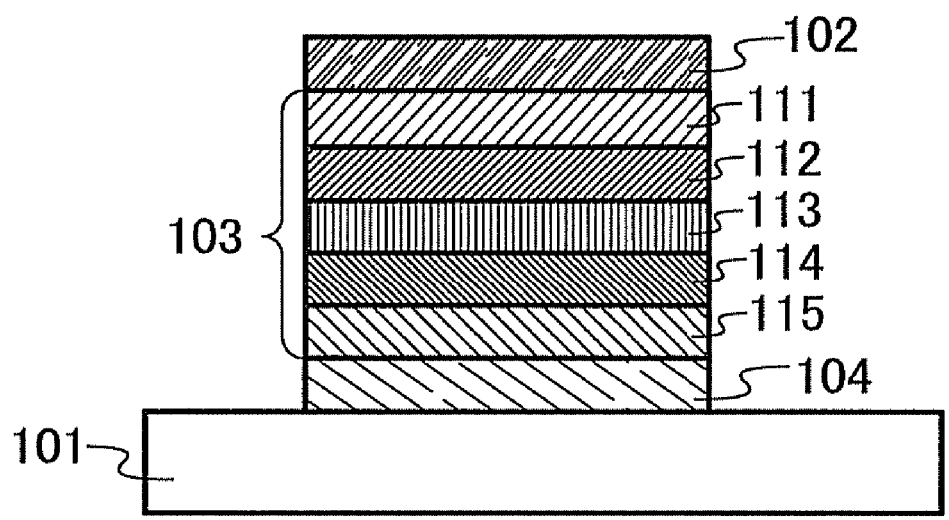
FIG. 2 illustrates a light-emitting element according to an embodiment of the present invention.

In addition, as illustrated in FIG. 2, over the substrate 101, the second electrode 104 functioning as a cathode, the EL layer 103, and the first electrode 102 functioning as an anode may be stacked in that order. In FIG. 2, a structure is employed in which the electron-injecting layer 115, the electron-transporting layer 114, the light-emitting layer 113, the hole-transporting layer 112, and the hole-injecting layer 111 are stacked in that order over the second electrode 104.

Note that in Embodiment 2, the light-emitting element is fabricated over a substrate formed using glass, plastic, or the like. By fabrication of a plurality of such light-emitting elements over one substrate, a passive matrix light-emitting device can be manufactured. Moreover, the light-emitting element may be fabricated over an electrode that is electrically connected to, for example, a thin film transistor (TFT) formed over a substrate formed using glass, plastic, or the like. Thus, an active matrix light-emitting device in which driving of a light-emitting element is controlled by a TFT can be manufactured. Note that there is no limitation on the structure of a TFT, and either a staggered TFT or an inverted staggered TFT may be used. Further, a driving circuit formed over a TFT substrate may be formed using an n-channel TFT and a p-channel TFT, or may be formed using any one of an n-channel TFT or a p-channel TFT. Furthermore, there is no limitation on the crystallinity of a semiconductor film used for the TFT. Either an amorphous semiconductor film or a crystalline semiconductor film may be used for the TFT. In addition, a single crystalline semiconductor film may be used. The single crystalline semiconductor film can be formed by a Smart Cut (registered trademark) method or the like.

Since the acenaphthoquinoxaline derivative described in Embodiment 1 easily receives electrons and has an electron-transporting property, the acenaphthoquinoxaline derivative can be suitably used for the light-emitting element. By using the acenaphthoquinoxaline derivative described in Embodiment 1, a light-emitting element with low driving voltage and/or low power consumption can be obtained.

Specifically, the acenaphthoquinoxaline derivative described in Embodiment 1 can be suitably used for the electron-transporting layer of the light-emitting element. By using the acenaphthoquinoxaline derivative described in Embodiment 1, a light-emitting element with low driving voltage and/or low power consumption can be obtained.

Further, since the acenaphthoquinoxaline derivative described in Embodiment 1 easily receives electrons and has an electron-transporting property, the acenaphthoquinoxaline derivative can be used for the electron-injecting layer. By using the acenaphthoquinoxaline derivative described in Embodiment 1 for the electron-injecting layer, a light-emitting element with low driving voltage and/or low power consumption can be obtained.

Further, since the acenaphthoquinoxaline derivative described in Embodiment 1 exhibits a light-emitting property, the acenaphthoquinoxaline derivative can be used as a substance having a high light-emitting property for the light-emitting layer. By using the acenaphthoquinoxaline derivative described in Embodiment 1 as a substance having a high light-emitting property, a blue to green light-emitting element can be obtained.

Further, the acenaphthoquinoxaline derivative described in Embodiment 1 can be used as a substance (a host material) into which a substance having a high light-emitting property is dispersed. By using the acenaphthoquinoxaline derivative described in Embodiment 1 as a host material, the electron-transporting property of the light-emitting layer can be improved, and thus carrier balance in the light-emitting layer can be controlled.

Note that Embodiment 2 can be combined with any other embodiment as appropriate.

Embodiment 3

Figure 3:
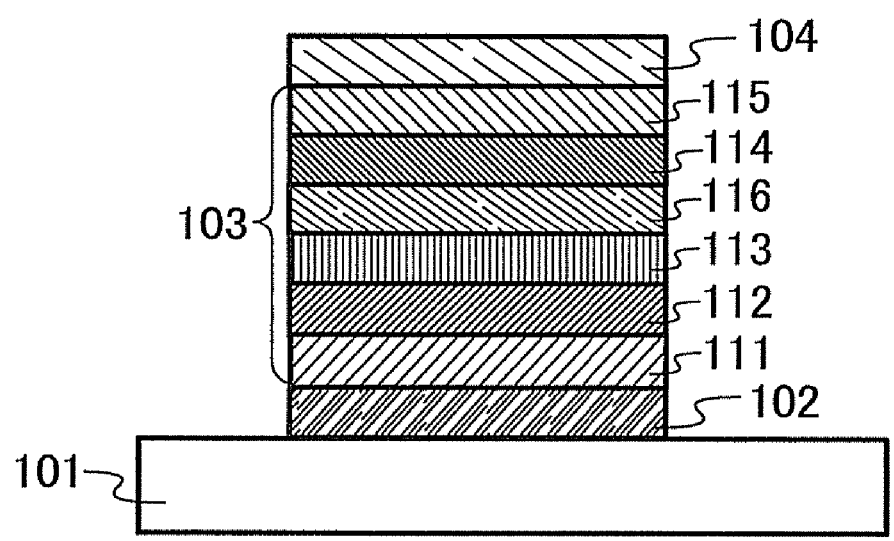
FIG. 3 illustrates a light-emitting element according to an embodiment of the present invention.

In Embodiment 3, as an embodiment of a light-emitting element according to the present invention, a structure that is different from the structure in Embodiment 2 is described using FIG. 3.

A light-emitting element illustrated in FIG. 3 includes the EL layer 103 between the first electrode 102 and the second electrode 104. The EL layer 103 includes the hole-injecting layer 111, the hole-transporting layer 112, the light-emitting layer 113, a layer 116 for controlling transport of electrons, the electron-transporting layer 114, and the electron-injecting layer 115.

Structures that are similar to those described in Embodiment 2 can be applied to the first electrode 102, the second electrode 104, the hole-injecting layer 111, the hole-transporting layer 112, the light-emitting layer 113, the electron-transporting layer 114, and the electron-injecting layer 115.

The layer 116 for controlling transport of electrons includes a first organic compound and a second organic compound, and the amount of the first organic compound is larger than the amount of the second organic compound. That is, the second organic compound is dispersed into the first organic compound. Further, the layer for controlling transport of electrons is preferably provided closer to the second electrode 104 functioning as a cathode than the light-emitting layer 113 is. That is, the layer for controlling transport of electrons is preferably provided between the light-emitting layer 113 and the second electrode 104.

When the layer for controlling transport of electrons is provided between the light-emitting layer and the second electrode 104 functioning as a cathode, the first organic compound is preferably an organic compound having an electron-transporting property. That is, the first organic compound is preferably a compound in which the electron-transporting property is higher than the hole-transporting property.

On the other hand, the second organic compound is preferably an organic compound having the function of trapping electrons. That is, the second organic compound preferably has a lowest unoccupied molecular orbital (LUMO) level that is lower than that of the first organic compound by 0.3 eV or more.

With the second organic compound included in the layer for controlling transport of electrons, the rate of transport of electrons in the whole layer is lower than the case where only the first organic compound is included in this layer. That is, by addition of the second organic compound, transport of carriers can be controlled. Further, by control of the concentration of the second organic compound, the rate of transport of carriers can be controlled. Specifically, the concentration of the second organic compound is preferably in the range of 0.1 to 5 wt % or in the range of 0.1 to 5 mol %.

Since the acenaphthoquinoxaline derivative described in Embodiment 1 easily receives electrons and has a lowest unoccupied molecular orbital (LUMO) level that is low, the acenaphthoquinoxaline derivative can be used as an electron-trapping material.

Figure 4:
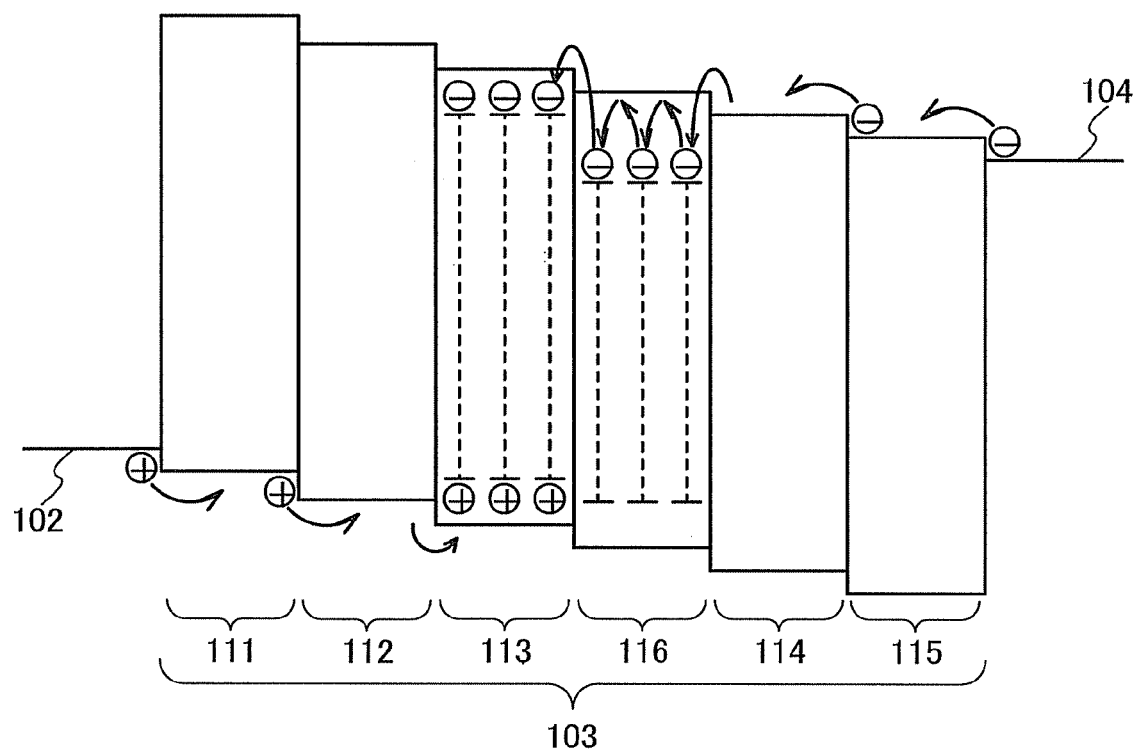
FIG. 4 illustrates a light-emitting element according to an embodiment of the present invention.

FIG. 4 is an example of a band diagram of the light-emitting element described in Embodiment 3. In FIG. 4, holes injected from the first electrode 102 into the light-emitting layer 113 through the hole-injecting layer 111 and the hole-transporting layer 112. On the other hand, electrons injected from the second electrode 104 into the layer 116 for controlling transport of electrons through the electron-injecting layer 115 and the electron-transporting layer 114. Transport of the electrons injected into the layer for controlling transport of electrons is slowed by the second organic compound having an electron trapping property. The electrons transported at a slower rate are injected into the light-emitting layer 113 and recombined with holes, whereby light is emitted.

In a conventional element structure in which the layer for controlling transport of electrons is not provided, electrons injected from the second electrode into the light-emitting layer through the electron-injecting layer and the electron-transporting layer. When the light-emitting layer has an electron-transporting property, i.e., when a material the amount of which is the largest in the light-emitting layer has an electron-transporting property, the electrons injected into the light-emitting layer could probably reach the hole-transporting layer by being transported through the light-emitting layer. The electrons that have reached the hole-transporting layer cause deterioration of the material included in the hole-transporting layer, which leads to deterioration of the light-emitting element.

However, by providing the layer for controlling transport of electrons, which is described in Embodiment 3, reaching the hole-transporting layer by electrons transported through the light-emitting layer can be suppressed. Accordingly, deterioration of the hole-transporting layer which is caused by the electrons that reach the hole-transporting layer can be suppressed. Thus, deterioration of the light-emitting element can be suppressed, whereby the lifetime of the element can be prolonged.

In the light-emitting element of Embodiment 3, the emission color of a substance having a high light-emitting property which is included in the light-emitting layer and the emission color of the second organic compound are preferably similar colors. This can keep the color purity of the light-emitting element even if the second organic compound unintendedly emits light. However, the second organic compound does not necessarily emit light. For example, in the case where emission efficiency of the substance having a high light-emitting property is higher, the concentration of the second organic compound in the layer 116 for controlling transport of electrons is preferably adjusted so that light emission from substantially only the substance having a high light-emitting property can be obtained (the concentration of the second organic compound is slightly reduced so that light emission from the second organic compound can be suppressed). In this case, the emission color of the substance having a high light-emitting property and the emission color of the second organic compound are similar colors (i.e., they have about the same or substantially the same level of energy gap). Therefore, energy is difficult to transfer from the substance having a high light-emitting property toward the second organic compound, whereby high emission efficiency can be obtained.

Alternatively, the second organic compound preferably emits light at a shorter wavelength than the substance having a high light-emitting property which is included in the light-emitting layer. That is, the peak wavelength of the second organic compound is preferably shorter than the peak wavelength of the substance having a high light-emitting property which is included in the light-emitting layer. In that case, the energy gap of the second organic compound is larger than the energy gap of the substance having a high light-emitting property. Accordingly, energy is difficult to transfer from the substance having a high light-emitting property toward the second organic compound; therefore, unintended light emission from the second organic compound can be suppressed.

Since the emission color of the acenaphthoquinoxaline derivative described in Embodiment 1 is blue to green, the emission color of the substance having a high light-emitting property which is included in the light-emitting layer of Embodiment 3 is preferably at a longer wavelength than the emission color of the acenaphthoquinoxaline derivative described in Embodiment 1. For example, as the substance having a high light-emitting property, it is preferable to use 2PCAPA, 2PCABPhA, 2DPAPA, 2DPABPhA, 2YGABPhA, or DPhAPhA, which emits green light, rubrene or BPT, which emits yellow light, p-mPhTD or p-mPhAFD, which emits red light, or the like.

Further, the first organic compound included in the layer 116 for controlling transport of electrons is an organic compound having an electron-transporting property. That is, the first organic compound is a compound in which the electron-transporting property is higher than the hole-transporting property. Specifically, the following substances can be used: metal complexes such as Alq, Almq$_3$, BeBq$_2$, BAlq, Znq, BAlq, ZnPBO, and ZnBTZ, heterocyclic compounds such as PBD, OXD-7, TAZ, TPBI, BPhen, and BCP, and condensed aromatic compounds such as CzPA, DPCzPA, DPPA, DNA, t-BuDNA, BANT, DPNS, DPNS2, and TPB3. Among them, metal complexes that are stable against electrons are preferably used.

Alternatively, a high molecular compound such as poly[(9, 9-dihexylfluorene-2,7-diyl)-co-(pyridine-3,5-diyl)] (abbreviation: PF-Py) or poly[(9,9-dioctylfluorene-2,7-diyl)-co-(2, 2'-bipyridine-6,6'-diyl)] (abbreviation: PF-BPy) can be used.

Further, as mentioned earlier, the LUMO level of the second organic compound is preferably lower than the LUMO level of the first organic compound by 0.3 eV or more. Therefore, a substance for the first organic compound may be selected as appropriate so as to satisfy such a condition, according to the LUMO level of the acenaphthoquinoxaline derivative described in Embodiment 1. For example, by using Alq for the first organic compound, the above condition can be satisfied.

Further, the thickness of the layer 116 for controlling transport of electrons is preferably greater than or equal to 5 nm and less than or equal to 20 nm. If the layer 116 is too thick, transport of carriers is slowed too much, resulting in an increase in driving voltage. Alternatively, if the layer 116 is too thin, the function of controlling transport of carriers cannot be achieved. Therefore, the thickness of the layer 116 is preferably greater than or equal to 5 nm and less than or equal to 20 nm.

Furthermore, since the layer for controlling transport of electrons controls transport of electrons, the layer is preferably provided between the light-emitting layer and the electrode functioning as a cathode. By providing the layer for controlling transport of electrons to be in contact with the light-emitting layer, injection of electrons into the light-emitting layer can be directly controlled. Accordingly, a change in the carrier balance in the light-emitting layer over time can be more suppressed, whereby a larger effect on improving the lifetime of the light-emitting element can be obtained. Furthermore, the process can be simplified.

Further, the layer for controlling transport of electrons is preferably provided so as to be in contact with the light-emitting layer. In such a case, the first organic compound included in the layer for controlling transport of electrons is preferably different in kind from an organic compound the amount of which is large in the light-emitting layer. In particular, in the case where the light-emitting layer includes a substance (a host material) into which a substance having a high light-emitting property is dispersed and the substance having a high light-emitting property (a guest material), the host material and the first organic compound are preferably different in kind from each other. With such a structure, transport of electrons from the layer for controlling transport of electrons to the light-emitting layer can be suppressed also between the first organic compound and the host material. Accordingly, the effect obtained by providing the layer for controlling transport of electrons can be further increased.

Note that a layer may be formed between the light-emitting layer 113 and the layer 116 for controlling transport of electrons.

For example, in a conventional light-emitting element where the layer 116 for controlling transport of electrons is not provided, holes injected from the first electrode 102 into the light-emitting layer 113 through the hole-injecting layer 111 and the hole-transporting layer 112 without slowing; accordingly, some of the holes reach the vicinity of the interface between the electron-transporting layer 114 and the light-emitting layer 113. If the holes then reach the electron-transporting layer 114, they could probably cause deterioration of the electron-transporting layer 114. Further, if the amount of holes that reach the electron-transporting layer 114 is increased due to this deterioration over time, recombination probability in the light-emitting layer 113 is decreased over time, which leads to a reduction in the lifetime of the element (luminance decay over time).

On the other hand, in the light-emitting element described in Embodiment 3, the layer 116 for controlling transport of electrons is provided. Accordingly, electrons injected from the second electrode 104 into the layer 116 for controlling transport of electrons through the electron-injecting layer 115 and the electron-transporting layer 114. Here, the layer 116 for controlling transport of electrons has a structure in which the second organic compound having an electron-trapping property is added to the first organic compound having an electron-transporting property. Accordingly, transport of the electrons injected into the layer 116 is slowed, and thus injection of electrons into the light-emitting layer 113 is controlled. As a result, it is unlikely that electrons will reach the hole-transporting layer 112 and then make it deteriorate. Similarly, it is highly unlikely that holes will reach the electron-transporting layer 114 and then make it deteriorate, because the layer 116 for controlling transport of electrons includes the first organic compound having an electron-transporting property. Note that it is important in the present invention that, instead of just applying a substance with low electron mobility to the layer 116 for controlling transport of electrons, an organic compound that reduces the electron-transporting property is added to an organic compound having an electron-transporting property. With such a structure, it becomes possible not only to control injection of electrons into the light-emitting layer 113 but also to suppress changes in the controlled amount of injected electrons over time.

As described above, by controlling the amount of electrons injected into the light-emitting layer, a phenomenon that the carrier balance is lost and then reduces recombination probability over time can be prevented. This leads to an improvement of the lifetime of the element (suppression of luminance decay over time).

Further, since the layer for controlling carrier transport, which is described in Embodiment 3, includes two or more kinds of substances, by controlling the combination or mixture ratio of the substances, the thickness of each layer, etc., the carrier balance can be precisely controlled.

Further, since the carrier balance can be controlled by controlling the combination or mixture ratio of the substances, the thickness of each layer, etc., the carrier balance can be controlled more easily than a conventional case. In other words, even without any change in the physical properties of the substances that are used, the carrier transport can be controlled with a mixture ratio of the substances, the thickness of each layer, etc.

Further, by using the organic compound the amount of which is the smallest in the two or more kinds of substances included in the layer for controlling carrier transport, the carrier transport is controlled. That is, the carrier transport can be controlled with the component the amount of which is the smallest in the components included in the layer for controlling carrier transport, which does not easily cause a change over time; accordingly, the lifetime of the light-emitting element can be prolonged. In other words, the carrier balance is unlikely to change than the case where it is controlled with one substance. For example, when the carrier transport is controlled with a layer formed using one substance, a partial change in morphology, partial crystallization, or the like results in a change in the balance in the whole layer, which causes sensitivity to a change over time. On the other hand, by controlling the carrier transport with the component the amount of which is the smallest in the components included in the layer for controlling carrier transport, as described in Embodiment 3, a change in morphology, crystallization, aggregation, or the like has less effect, which does not easily cause a change over time. Thus, a light-emitting element with long lifetime can be obtained in which the carrier balance does not easily decrease over time and accordingly emission efficiency is unlikely to decrease over time.

Since the acenaphthoquinoxaline derivative described in Embodiment 1 easily receives electrons and has a lowest unoccupied molecular orbital (LUMO) level that is low, the acenaphthoquinoxaline derivative can be used as an electron-trapping material. By applying the acenaphthoquinoxaline derivative described in Embodiment 1 to the layer for controlling transport of electrons which is described in Embodiment 3, a light-emitting element with long lifetime can be obtained in which emission efficiency does not easily change over time.

Note that Embodiment 3 can be combined with any other embodiment as appropriate.

Embodiment 4

In Embodiment 4, an embodiment of a light-emitting element in which a plurality of light-emitting units according to the present invention are stacked (hereinafter, referred to as a stacked type element) is described with reference to FIG. 5. This light-emitting element is a stacked-type element including a plurality of light-emitting units between a first electrode and a second electrode. The structure of each of the light-emitting unit can be similar to that described in Embodiment 2 or Embodiment 3. In other words, the light-emitting element described in Embodiment 2 or Embodiment 3 is a light-emitting element having one light-emitting unit. In Embodiment 4, a light-emitting element having a plurality of light-emitting units will be described.

Figure 5:
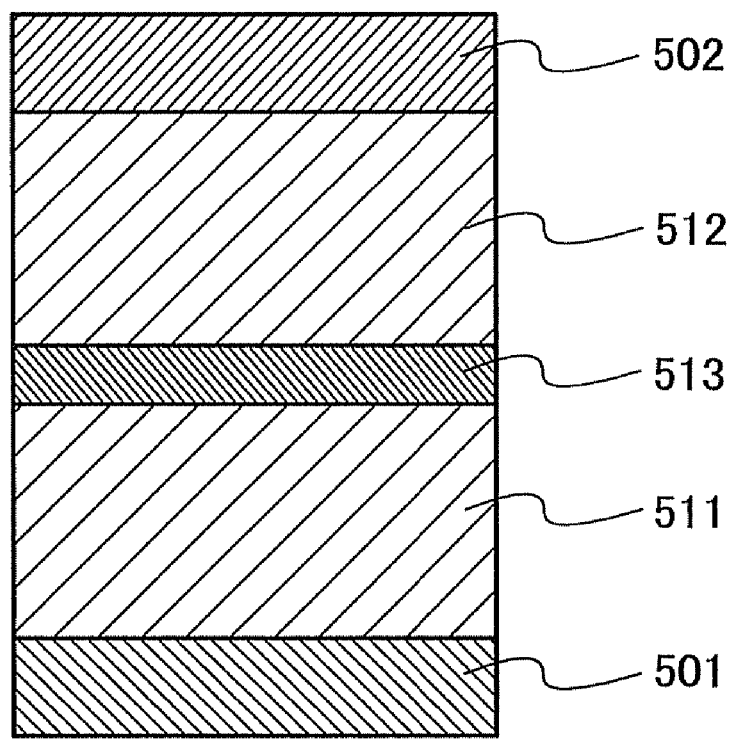
FIG. 5 illustrates a light-emitting element according to an embodiment of the present invention.

In FIG. 5, a first light-emitting unit 511 and a second light-emitting unit 512 are stacked between a first electrode 501 and a second electrode 502, and a charge-generating layer 513 is provided between the first light-emitting unit 511 and the second light-emitting unit 512. Electrodes that are similar to the electrodes of Embodiment 2 can be applied to the first electrode 501 and the second electrode 502. Further, the first light-emitting unit 511 and the second light-emitting unit 512 may have either the same or different structure, which can be similar to those described in Embodiment 2.

The charge-generating layer 513 is a layer that injects electrons into a light-emitting unit on one side and injects holes into a light-emitting unit on the other side when a voltage is applied to the first electrode 501 and the second electrode 502, and may be either a single layer or a stack of plural layers. As a stack structure of plural layers, a structure in which a layer that injects holes and a layer that injects electrons are stacked is preferable.

As the layer that injects holes, a semiconductor or an insulator, such as molybdenum oxide, vanadium oxide, rhenium oxide, or ruthenium oxide, can be used. Alternatively, a structure may be employed in which an acceptor substance is added to a substance having a high hole-transporting property. The layer including a substance having a high hole-transporting property and an acceptor substance is formed using the composite material described in Embodiment 2 and includes, as the acceptor substance, 7,7,8,8-tetracyano-2,3,5,6-tetrafluoroquinodimethane (abbreviation: $F_4$-TCNQ) or metal oxide such as vanadium oxide, molybdenum oxide, or tungsten oxide. As the substance having a high hole-transporting property, any of a variety of compounds such as aromatic amine compounds, carbazole derivatives, aromatic hydrocarbons, or high molecular compounds (oligomers, dendrimers, polymers, etc.) can be used. Note that a substance having a hole mobility of $10^{-6}$ cm$^2$/Vs or more is preferably applied to the substance having a high hole-transporting property. However, any other substance may also be used as long as it is a substance in which the hole-transporting property is higher than the electron-transporting property. Since the composite material of the substance having a high hole-transporting property and the acceptor substance has an excellent carrier-injecting property and an excellent carrier-transporting property, low-voltage driving and low-current driving can be realized.

As the layer that injects electrons, an insulator or a semiconductor, such as lithium oxide, lithium fluoride, or cesium carbonate, can be used. Alternatively, a structure may be employed in which a donor substance is added to a substance having a high electron-transporting property. As the donor substance, an alkali metal, an alkaline earth metal, a rare earth metal, a metal belonging to Group 13 of the periodic table, or an oxide or carbonate thereof can be used. Specifically, lithium (Li), cesium (Cs), magnesium (Mg), calcium (Ca), ytterbium (Yb), indium (In), lithium oxide, cesium carbonate, or the like is preferably used. Alternatively, an organic compound such as tetrathianaphthacene may be used as the donor substance. As the substance having a high electron-transporting property, the materials described in Embodiment 1 can be used. Note that a substance having an electron mobility of $10^{-6}$ cm$^2$/Vs or more is preferably applied to the substance having a high electron-transporting property. However, any other substance may also be used as long as it is a substance in which the electron-transporting property is higher than the hole-transporting property. Since the composite material of the substance having a high electron-transporting property and the donor substance has an excellent carrier-injecting property and an excellent carrier-transporting property, low-voltage driving and low-current driving can be realized.

Further, for the charge-generating layer 513, the electrode materials described in Embodiment 2 can be used. For example, the charge-generating layer 513 may be formed using a layer including a substance having a hole-transporting property and metal oxide in combination with a transparent conductive film. Note that the charge-generating layer is preferably a layer having a high light-transmitting property in terms of light extraction efficiency.

In any case, the charge generation layer 513 interposed between the first light-emitting unit 511 and the second light-emitting unit 512 may have any structure as long as electrons can be injected into the light-emitting unit on one side and holes can be injected into the light-emitting unit on the other side when a voltage is applied between the first electrode 501 and the second electrode 502. For example, any structure is acceptable as long as the charge generation layer 513 injects electrons into the first light-emitting unit 511 and injects holes into the second light-emitting unit 512 when a voltage is applied so that the potential of the first electrode is higher than that of the second electrode.

In Embodiment 4, the light-emitting element having two light-emitting units is described. However, the present invention can be applied to a light-emitting element in which three or more light-emitting units are stacked, in a similar manner. As in the light-emitting element according to Embodiment 4, by arranging a plurality of light-emitting units between a pair of electrodes so that the plurality of light-emitting units can be partitioned by a charge generation layer, light emission in a high luminance region can be achieved with current density kept low; thus, a light-emitting element having long life can be realized. Further, when the light-emitting element is applied to a lighting apparatus, voltage drop due to the resistance of the electrode materials can be suppressed; thus, uniform light emission in a large area can be achieved. Furthermore, a light-emitting device capable of low-voltage driving with low power consumption can be realized.

Further, by forming light-emitting units to emit light of different colors from each other, a light-emitting element as a whole can provide light emission of a desired color. For example, by forming a light-emitting element having two light-emitting units such that the emission color of the first light-emitting unit and the emission color of the second light-emitting unit are complementary to each other, the light-emitting element can provide white light emission as a whole. Note that "complementary colors" refer to colors that can produce an achromatic color when mixed. That is, when light emitted from substances that emit light of complementary colors is mixed, white light emission can be obtained. Further, the same can be applied to a light-emitting element having three light-emitting units. For example, the light-emitting element as a whole can provide white light emission when the emission color of the first light-emitting unit is red, the emission color of the second light-emitting unit is green, and the emission color of the third light-emitting unit is blue.

Note that Embodiment 4 can be combined with any other embodiment as appropriate.

Embodiment 5

In Embodiment 5, a light-emitting device having a light-emitting element of the present invention will be described.

In Embodiment 5, a light-emitting device having any of the light-emitting elements described in Embodiments 2 to 4 in a pixel portion is described using FIGS. 6A and 6B. Note that FIG. 6A is a top view illustrating the light-emitting device and FIG. 6B is a cross-sectional view of FIG. 6A taken along lines A-A' and B-B' This light-emitting device includes a driver circuit portion (a source side driver circuit) 601, a pixel portion 602, and a driver circuit portion (a gate side driver circuit) 603, which are indicated by dotted lines, in order to control the light emission from the light-emitting element. Further, reference numeral 604 denotes a sealing substrate and reference numeral 605 denotes a sealing material. Reference numeral 607 denotes a space surrounded by the sealing material 605.

Note that a leading wiring 608 is a wiring for transmitting signals that are input to the source side driver circuit 601 and the gate side driver circuit 603. The leading wiring 608 receives video signals, clock signals, start signals, reset signals, and the like from an flexible printed circuit (FPC) 609 serving as an external input terminal. Note that although only an FPC is illustrated here, this FPC may be provided with a printed wiring board (PWB). The light-emitting device in this specification includes not only a light-emitting device itself but also a light-emitting device to which an FPC or a PWB is attached.

Then, a cross-sectional structure is described using FIG. 6B. The driver circuit portions and the pixel portion are provided over an element substrate 610, but only the source side driver circuit 601, which is the driver circuit portion, and one pixel of the pixel portion 602 are illustrated.

Further, a CMOS circuit which is a combination of an n-channel TFT 623 and a p-channel TFT 624 is formed in the source side driver circuit 601. The driver circuit may be formed using various types of circuits such as CMOS circuits, PMOS circuits, or NMOS circuits. Furthermore, in Embodiment 5, a driver-integrated type in which a driver circuit is formed over a substrate provided with a pixel portion is described; however, the present invention is not limited to this type, and the driver circuit can be formed outside the substrate instead of being formed over the substrate provided with the pixel portion.

Further, the pixel portion 602 includes a plurality of pixels each having a switching TFT 611, a current controlling TFT 612, and a first electrode 613 which is electrically connected to a drain of the current controlling TFT 612. Note that an insulator 614 is formed to cover an end portion of the first electrode 613. Here, a positive photosensitive acrylic resin film is used to form the insulator 614.

Further, in order to improve coverage, the insulator 614 is provided such that either an upper end portion or a lower end portion of the insulator 614 has a curved surface with a curvature. For example, when positive photosensitive acrylic is used as a material for the insulator 614, it is preferable that only an upper end portion of the insulator 614 have a curved surface with a radius of curvature (0.2 to 3 µm). Alternatively, the insulator 614 can be formed using either a negative type that becomes insoluble in an etchant by light irradiation or a positive type that becomes soluble in an etchant by light irradiation.

An EL layer 616 and a second electrode 617 are formed over the first electrode 613. Here, any of a variety of metals, alloys, electrically conductive compounds, or a mixture thereof can be used for a material of the first electrode 613. If the first electrode is used as an anode, it is preferable that the first electrode be formed using, among such materials, any of metals, alloys, or electrically conductive compounds, a mixture thereof or the like having a high work function (preferably, a work function of 4.0 eV or more) among such materials. For example, the first electrode 613 can be formed using a single-layer film such as an indium oxide-tin oxide film containing silicon, an indium oxide-zinc oxide film, a titanium nitride film, a chromium film, a tungsten film, a Zn film, a Pt film, or the like; a stack of a titanium nitride film and a film containing aluminum as the main component; or a three-layer structure of a titanium nitride film, a film containing aluminum as the main component, and a titanium nitride film. Note that with a stack structure, the first electrode 613 has low resistance as a wiring, forms a favorable ohmic contact, and can serve as an anode.

Further, the EL layer 616 is formed by various methods such as an evaporation method using an evaporation mask, an inkjet method, a spin coating method, or the like. The EL layer 616 includes the acenaphthoquinoxaline derivative described in Embodiment 1. Further, another material included in the EL layer 616, any of low molecular compounds or high molecular compounds (the category includes oligomers, dendrimers, polymers, etc.) may be used. Furthermore, the material used for the EL layer is not limited to an organic compound and may be an inorganic compound.

Further, as the material for the second electrode 617, various types of metals, alloys, or electrically conductive compounds, a mixture thereof, or the like can be used. If the second electrode is used as a cathode, it is preferable that the second electrode be formed using, among such materials, any of metals, alloys, or electrically conductive compounds, a mixture thereof, or the like having a low work function (preferably, a work function of 3.8 eV or less). For example, there are elements belonging to Group 1 and Group 2 of the periodic table, that is, alkali metals such as lithium (Li) and cesium (Cs); alkaline earth metals such as magnesium (Mg), calcium (Ca), and strontium (Sr); alloys containing any of these metals (e.g., MgAg and AlLi); and the like. When light generated in the EL layer 616 is transmitted through the second electrode 617, the second electrode 617 can also be formed using a stack of a thin metal film with a small thickness and a transparent conductive film (indium oxide-tin oxide (ITO), indium oxide-tin oxide containing silicon or silicon oxide, indium oxide-zinc oxide (IZO), indium oxide containing tungsten oxide and zinc oxide (IWZO), or the like).

Furthermore, by attaching the sealing substrate 604 and the element substrate 610 to each other with the sealing material 605, a light-emitting element 618 is provided in the space 607 surrounded by the element substrate 610, the sealing substrate 604, and the sealing material 605. Note that the space 607 is filled with a filler. Note that there are also cases where the space 607 may be filled with an inert gas (e.g., nitrogen or argon) as such a filler, or where the space 607 may be filled with the sealing material 605.

Note that as the sealing material 605, an epoxy-based resin is preferably used. In addition, it is preferable that such a material allows as little moisture or oxygen as possible to permeate. Further, as a material for the sealing substrate 604, a plastic substrate formed using fiberglass-reinforced plastics (FRP), polyvinyl fluoride (PVF), polyester, acrylic, or the like can be used instead of a glass substrate or a quartz substrate.

As described above, the light-emitting device including a light-emitting element according to the present invention can be obtained.

The light-emitting device described in Embodiment 5 includes the acenaphthoquinoxaline derivative described in Embodiment 1. The acenaphthoquinoxaline derivative described in Embodiment 1 easily receives electrons and has an electron-transporting property. Accordingly, by using the acenaphthoquinoxaline derivative described in Embodiment 1, a light-emitting device with lower power consumption and/or long lifetime can be obtained.

Figure 7A:
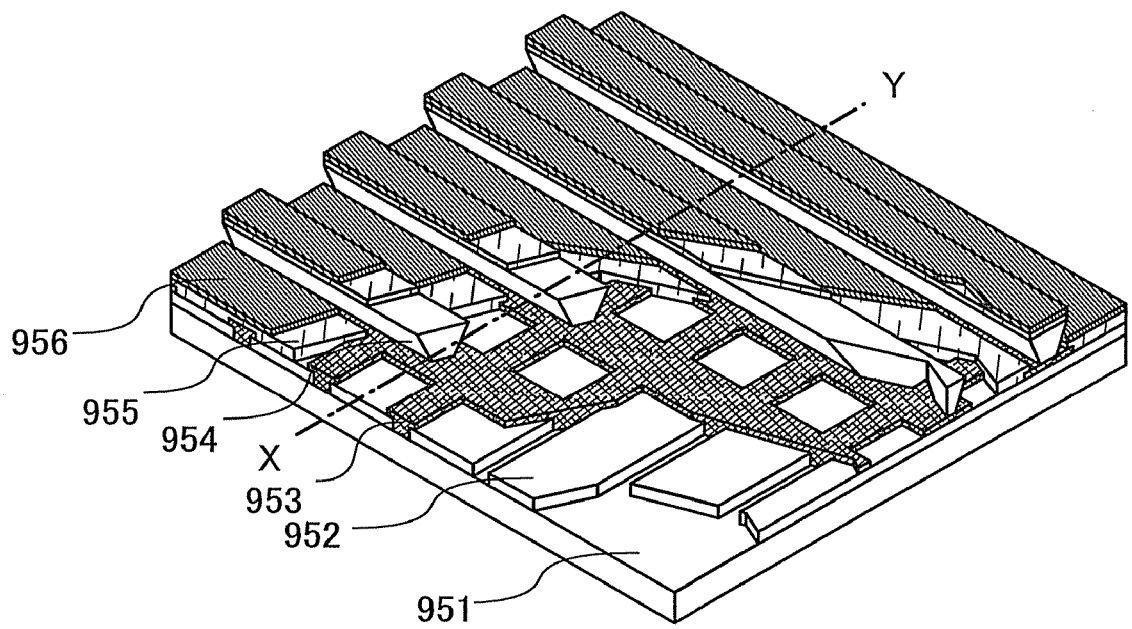
FIGS. 7A and 7B illustrate a light-emitting device according to an embodiment of the present invention.
Figure 7B:
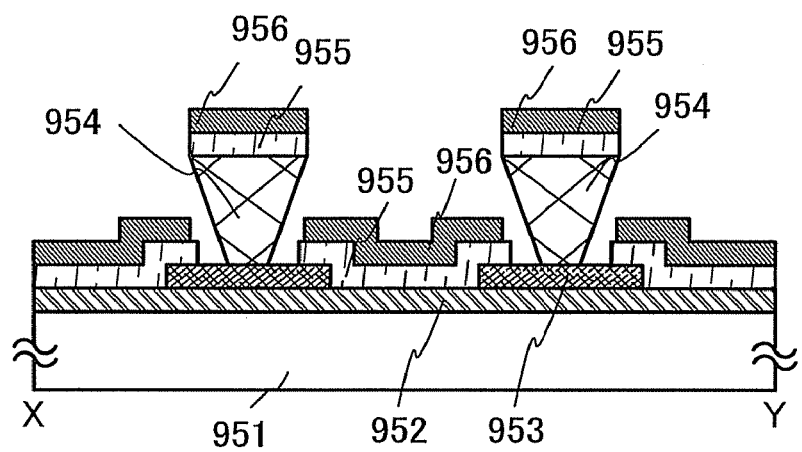

As described above, in Embodiment 5, although an active matrix light-emitting device which controls driving of a light-emitting element with a transistor is described, the light-emitting device may be a passive matrix light-emitting device. FIGS. 7A and 7B illustrate a passive matrix light-emitting device manufactured according to the present invention. Note that FIG. 7A is a perspective view of the light-emitting device and FIG. 7B is a cross-sectional view of FIG. 7A taken along a line X-Y. In FIGS. 7A and 7B, an EL layer 955 is provided between an electrode 952 and an electrode 956 over a substrate 951. An end portion of the electrode 952 is covered with an insulating layer 953. In addition, a partition layer 954 is provided over the insulating layer 953. The sidewalls of the partition layer 954 slope so that the distance between one sidewall and the other sidewall gradually decreases toward the surface of the substrate. In other words, a cross section taken along the direction of the short side of the partition layer 954 is trapezoidal, and the lower side (a side in contact with the insulating layer 953, which is one of a pair of parallel sides of the trapezoidal cross section) is shorter than the upper side (a side not in contact with the insulating layer 953, which is the other of the pair of parallel sides). Providing the partition layer 954 in this manner enables patterning of the EL layer 955 and the electrode 956. Further, also in the case of a passive matrix light-emitting device, by including a light-emitting element with low driving voltage which is according to the present invention, a light-emitting device with low power consumption and/or long lifetime can be obtained.

Note that Embodiment 5 can be combined with any other embodiment as appropriate.

Embodiment 6

In Embodiment 6, an electronic device of the present invention, which includes the light-emitting device described in Embodiment 5 as a part, is described. Electronic devices of the present invention include any of the light-emitting elements described in Embodiments 2 to 4 and a display portion with low power consumption and/or long lifetime.

As examples of the electronic devices of the present invention, there are televisions, cameras such as video cameras and digital cameras, goggle type displays (head-mounted displays), navigation systems, audio replay devices (e.g., car audio systems and audio systems), computers, game machines, portable information terminals (e.g., mobile computers, cellular phones, portable game machines, and electronic book readers), image replay devices in which a recording medium is provided (devices that are capable of replaying recording media such as digital versatile discs (DVDs) and equipped with a display device that can display an image), and the like. Specific examples of these electronic devices are illustrated in FIGS. 8A to 8D.

Figure 8A:
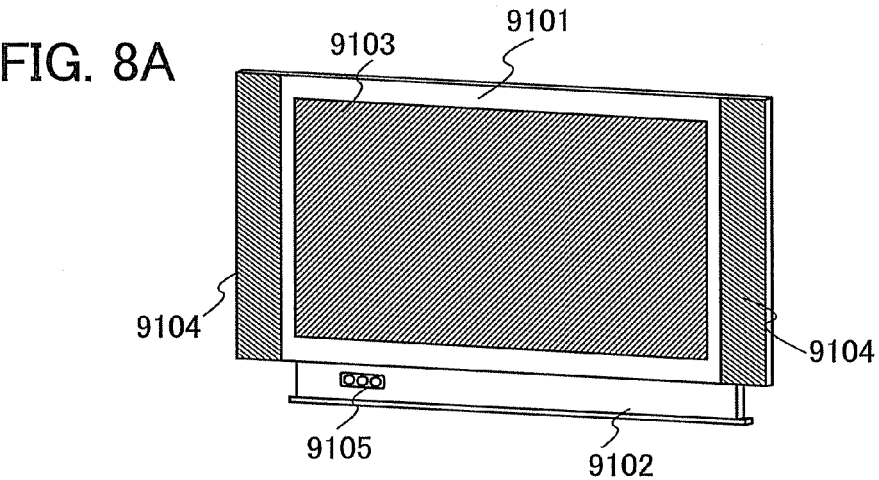
FIGS. 8A to 8D illustrate electronic devices according to an embodiment of the present invention.

FIG. 8A illustrates a television set according to Embodiment 6, which includes a housing 9101, a supporting base 9102, a display portion 9103, speaker portions 9104, a video input terminal 9105, and the like. In the display portion 9103 of this television set, light-emitting elements similar to those described in Embodiments 2 to 4 are arranged in matrix. The features of the light-emitting elements are low driving voltage, low power consumption, and long lifetime. Since the display portion 9103 including the light-emitting elements has features similar to those of the light-emitting elements, power consumption of this television set is reduced. With such features, power supply circuits in the television set can be greatly reduced or downsized; accordingly, a reduction in the size and weight of the housing 9101 or the supporting base 9102 can be achieved. In the television set according to Embodiment 6, a reduction in power consumption, size, and weight is achieved; thus, a product that is suitable for living environment can be provided. Further, the features of this television set include long lifetime, and thus a television set that can withstand long time use can be provided.

Figure 8B:
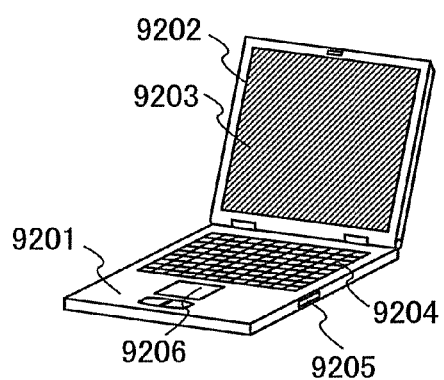

FIG. 8B illustrates a computer according to Embodiment 6, which includes a main body 9201, a housing 9202, a display portion 9203, a keyboard 9204, an external connection port 9205, a pointing device 9206, and the like. In the display portion 9203 of this computer, light-emitting elements similar to those described in Embodiments 2 to 4 are arranged in matrix. The features of the light-emitting element are low driving voltage, low power consumption, and long lifetime. Since the display portion 9203 including the light-emitting elements has features similar to those of the light-emitting elements, power consumption of this computer is reduced. With such features, power supply circuits in the computer can be greatly reduced or downsized; accordingly, a reduction in the size and weight of the main body 9201 and the housing 9202 can be achieved. In the computer according to Embodiment 6, a reduction in power consumption, size, and weight is achieved; thus, a product that is suitable for the environment can be provided. Further, the features of this computer include long lifetime, and thus a computer that can withstand long time use can be provided.

Figure 8C:
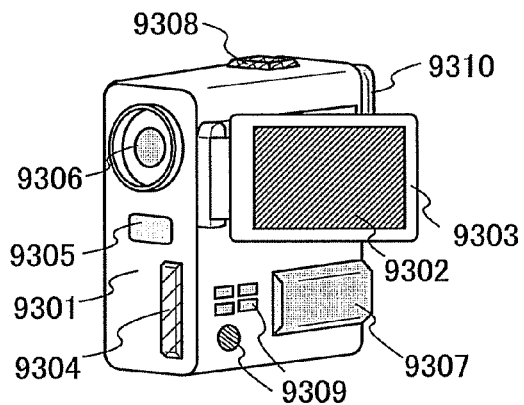

FIG. 8C illustrates a camera according to Embodiment 6, which includes a main body 9301, a display portion 9302, a housing 9303, an external connection port 9304, a remote control receiving portion 9305, an image receiving portion 9306, a battery 9307, an audio input portion 9308, operation keys 9309, an eyepiece portion 9310, and the like. In the display portion 9302 of this camera, light-emitting elements similar to those described in Embodiments 2 to 4 are arranged in matrix. The features of the light-emitting elements are low driving voltage, low power consumption, and long lifetime. Since the display portion 9302 including the light-emitting elements has features similar to those of the light-emitting elements, power consumption of this camera is reduced. With such features, power supply circuits in the camera can be greatly reduced or downsized; accordingly, a reduction in the size and weight of the main body 9301 can be achieved. In the camera according to Embodiment 6, a reduction in power consumption, size, and weight is achieved; thus, a product that is suitable for being carried can be provided. Further, the features of this camera include long lifetime, and thus a camera that can withstand long time use can be provided.

Figure 8D:
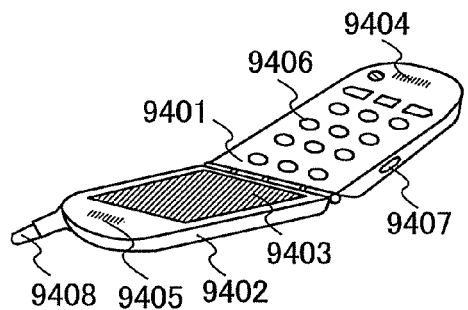

FIG. 8D illustrates a cellular phone according to Embodiment 6, which includes a main body 9401, a housing 9402, a display portion 9403, an audio input portion 9404, an audio output portion 9405, operation keys 9406, an external connection port 9407, an antenna 9408, and the like. In the display portion 9403 of this cellular phone, light-emitting elements similar to those described in Embodiments 2 to 4 are arranged in matrix. The features of the light-emitting elements are low driving voltage, low power consumption, and long lifetime. Since the display portion 9403 including the light-emitting elements has features similar to those of the light-emitting elements, power consumption of this cellular phone is reduced. With such features, power supply circuits in the cellular phone can be greatly reduced or downsized; accordingly, a reduction in the size and weight of the main body 9401 and the housing 9402 can be achieved. In the cellular phone according to Embodiment 6, a reduction in power consumption, size, and weight is achieved; thus, a product that is suitable for being carried can be provided. Further, the features of this cellular phone include long lifetime, and thus a cellular phone that can withstand long time use can be provided.

Figure 14A:
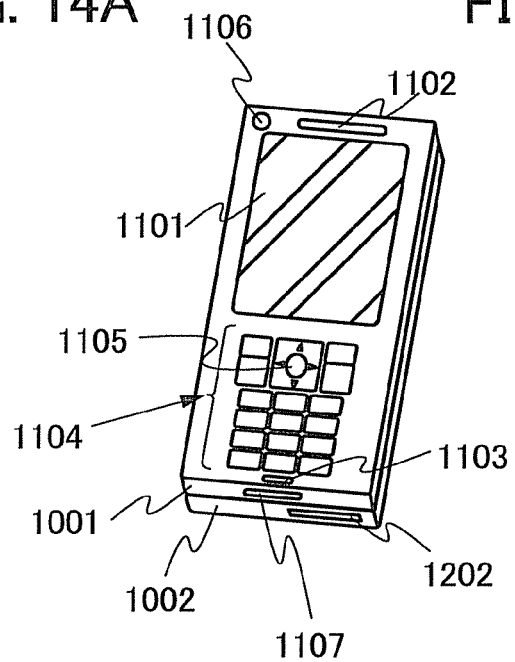
FIGS. 14A to 14C illustrate an electronic device according to an embodiment of the present invention.
Figure 14B:
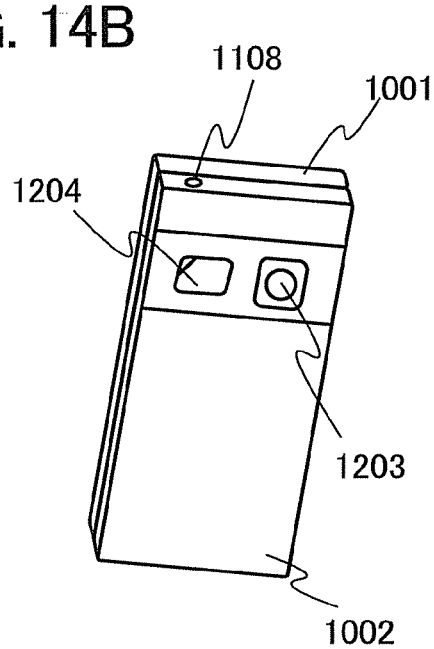
Figure 14C:
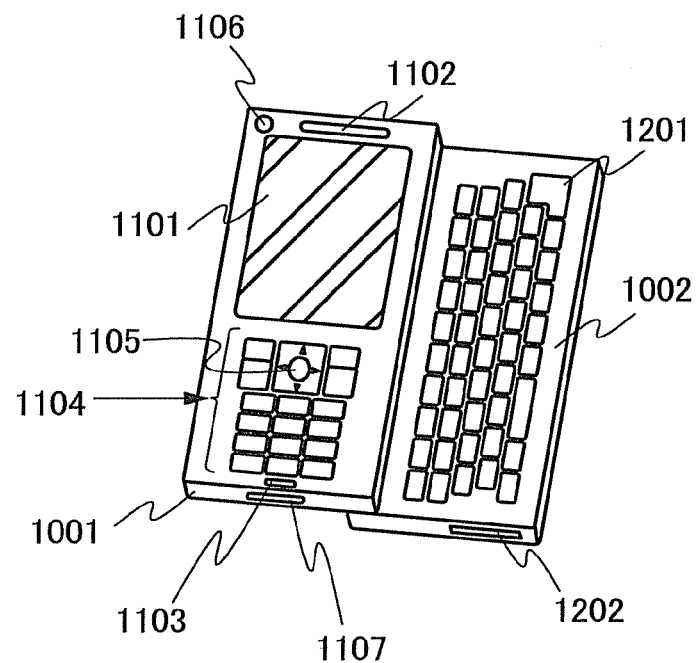

FIGS. 14A to 14C illustrate an example of a cellular phone having a structure, which is different from the structure of the cellular phone of FIG. 8D. FIG. 14A is a front view, FIG. 14B is a rear view, and FIG. 14C is a development view. The cellular phone in FIGS. 14A to 14C is a so-called smartphone which has both a function of a phone and a function of a portable information terminal, and incorporates a computer to conduct a variety of data processing in addition to voice calls.

The cellular phone illustrated in FIGS. 14A to 14C includes two housings 1001 and 1002. The housing 1001 includes a display portion 1101, a speaker 1102, a microphone 1103, operation keys 1104, a pointing device 1105, a camera lens 1106, an external connection terminal 1107, and the like, while the housing 1002 includes an earphone terminal 1108, a keyboard 1201, an external memory slot 1202, a camera lens 1203, a light 1204, and the like. In addition, an antenna is incorporated in the housing 1001.

In addition to the above structure, the cellular phone may incorporate a non-contact IC chip, a small-sized memory device, or the like.

In the display portion 1101, the light-emitting device described in Embodiment 5 can be incorporated, and a display direction can be changed as appropriate depending on the usage mode. Since the cellular phone is provided with the camera lens 1106 and the display portion 1101 on one surface, the cellular phone can be used as a videophone. Further, a still image or a moving image can be taken with the camera lens 1203 and the light 1204, using the display portion 1101 as a viewfinder. The speaker 1102 and the microphone 1103 can be used for video calls, recording, replaying, and the like without being limited to voice calls. With the use of the operation keys 1104, making and receiving calls, inputting simple information such as e-mail or the like, scrolling the screen, moving the cursor, or the like are possible. Furthermore, the housing 1001 and the housing 1002 (FIG. 14A) which are overlapped with each other can slide as illustrated in FIG. 14C, so that the cellular phone can be used as a portable information terminal. In this case, smooth operation can be conducted using the keyboard 1201 and the pointing device 1105. The external connection terminal 1107 can be connected to an AC adaptor and various types of cables such as a USB cable, and charging, data communication with a computer, or the like are possible. Furthermore, a large amount of data can be stored and moved by inserting a storage medium into the external memory slot 1202.

In addition to the above functions, the cellular phone may include an infrared communication function, a television receiving function, or the like.

Figure 9:
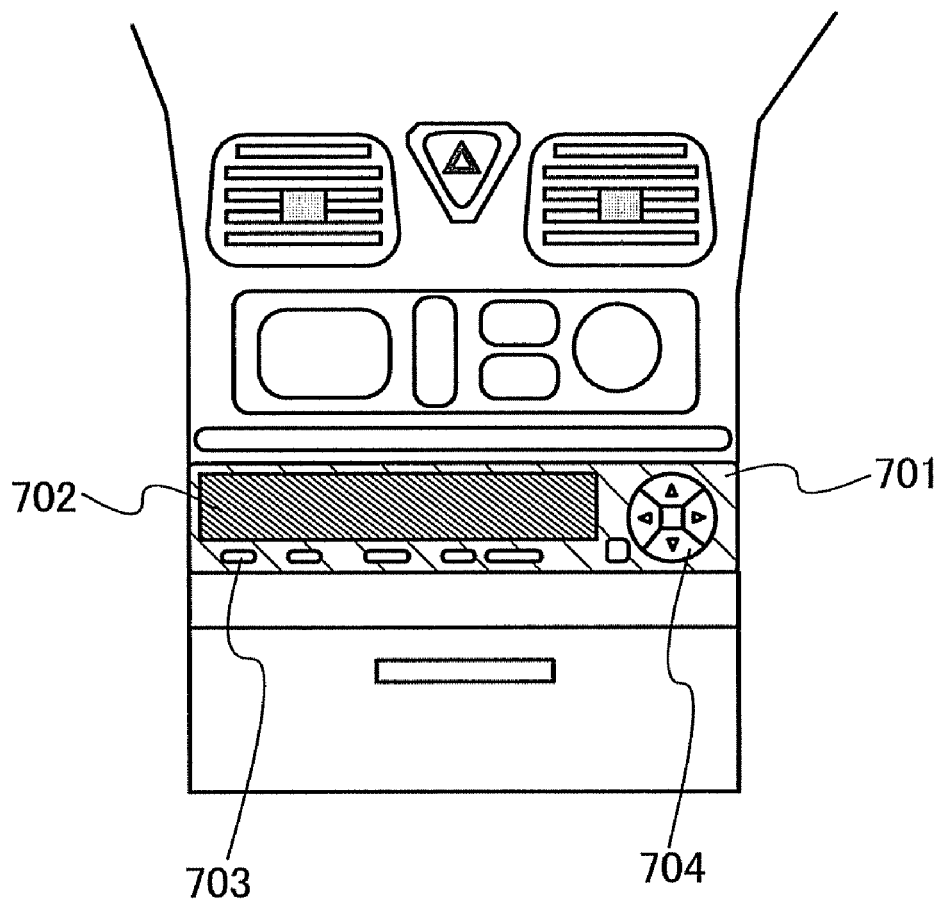
FIG. 9 illustrates an electronic device according to an embodiment of the present invention.

FIG. 9 illustrates an audio replay device, specifically, a car audio system which includes a main body 701, a display portion 702, and operation switches 703 and 704. The display portion 702 can be formed by using the light-emitting device (passive matrix type or active matrix type) of Embodiment 5. Further, this display portion 702 may be formed using a segment type light-emitting device. In any case, by using a light-emitting element according to the present invention, a display portion with low power consumption and high brightness can be formed with the use of a vehicle power source (12 to 42 V). Furthermore, although Embodiment 6 describes an in-car audio system, a light-emitting device according to the present invention may also be used in a portable audio system or an audio system for home use.

Figure 10:
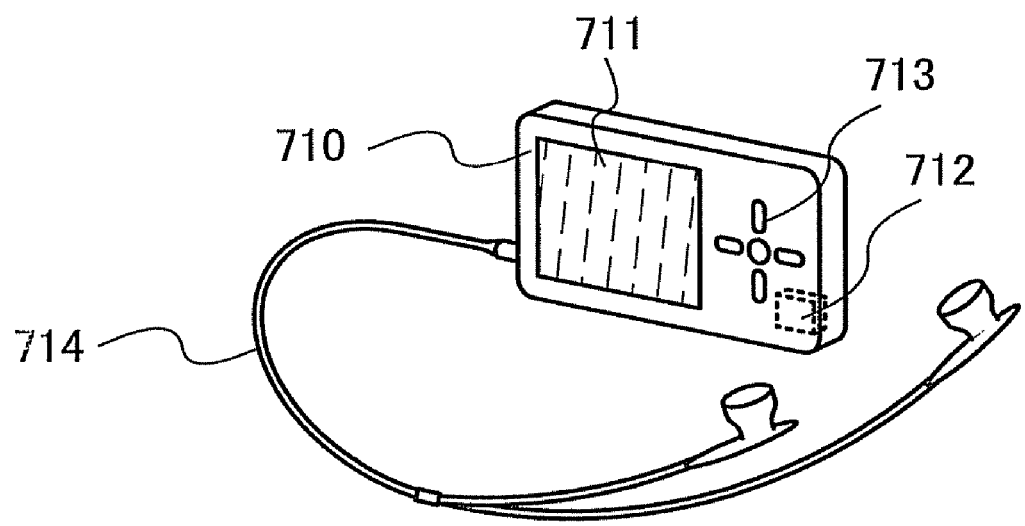
FIG. 10 illustrates an electronic device according to an embodiment of the present invention.

FIG. 10 illustrates a digital player as an example of an audio replay device. The digital player illustrated in FIG. 10 includes a main body 710, a display portion 711, a memory portion 712, an operation portion 713, a pair of earphones 714, and the like. Note that a pair of headphones or wireless earphones can be used instead of the pair of earphones 714. The display portion 711 can be formed by using the light-emitting device (passive matrix type or active matrix type) of Embodiment 5. Further, the display portion 711 may be formed using a segment type light-emitting device. In any case, the use of a light-emitting element according to the present invention makes it possible to form a display portion with low power consumption and high brightness, which can display images even when using a secondary battery (e.g., a nickel-hydrogen battery). As the memory portion 712, a hard disk or a nonvolatile memory is used. For example, by using a NAND-type nonvolatile memory with a recording capacity of 20 to 200 gigabytes (GB) and by operating the operating portion 713, an image or a sound (music) can be recorded and replayed. Note that in the display portion 702 and the display portion 711, white characters are displayed against a black background, and accordingly power consumption can be reduced. This is particularly effective for portable audio systems.

As described above, the applicable range of the light-emitting device manufactured by applying the present invention is wide so that the light-emitting device can be applied to electronic devices in a wide variety of fields. By applying the present invention, an electronic device that has a display portion with low power consumption can be manufactured. Further, an electronic device including a display portion with long lifetime which can withstand long time use can be provided.

A light-emitting device to which the present invention is applied includes a light-emitting element having high emission efficiency, and therefore can also be used as a lighting apparatus. One mode of using a light-emitting element to which the present invention is applied as a lighting apparatus is described using FIG. 11.

Figure 11:
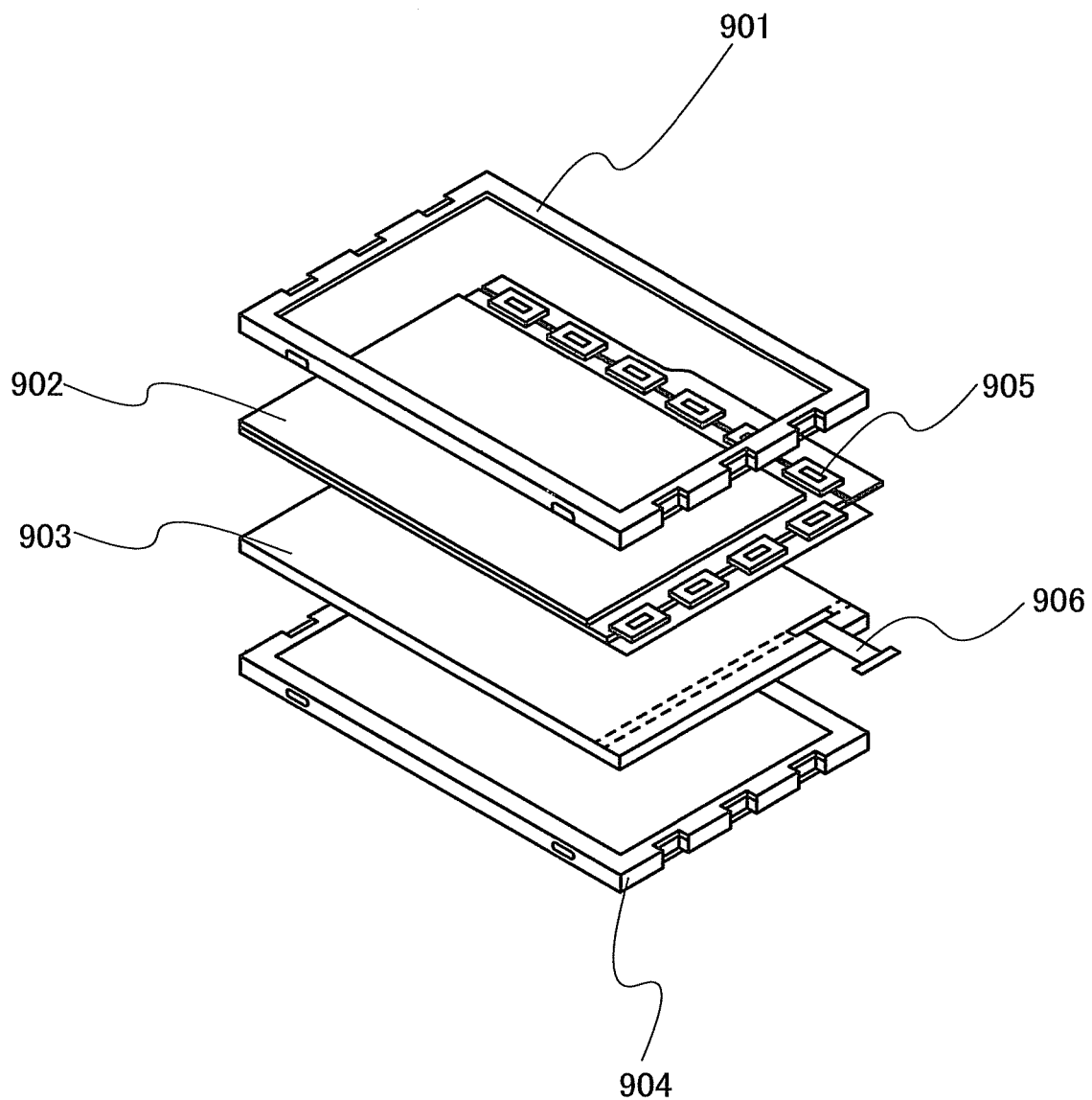
FIG. 11 illustrates an electronic device according to an embodiment of the present invention.

FIG. 11 illustrates a liquid crystal display device using a light-emitting device according to the present invention as a backlight, as an example of the electronic device using a light-emitting device according to the present invention as a lighting apparatus. The liquid crystal display device illustrated in FIG. 11 includes a housing 901, a liquid crystal layer 902, a backlight 903, and a housing 904, and the liquid crystal layer 902 is connected to a driver IC 905. Further, the light-emitting device to which the present invention is applied is used as the backlight 903, and a current is supplied through a terminal 906.

Because a light-emitting device according to the present invention is thin and its power consumption is low, the thickness and power consumption of a liquid crystal display device can be reduced by using a light-emitting device according to the present invention as a backlight of the liquid crystal display device. Moreover, a light-emitting device according to the present invention is a plane emission type lighting apparatus and can have a large area. Thus, the backlight can have a large area, and a liquid crystal display device having a large area can also be obtained. Furthermore, since a light-emitting device of the present invention has long lifetime, a liquid crystal display device with long lifetime can be obtained.

Figure 12:
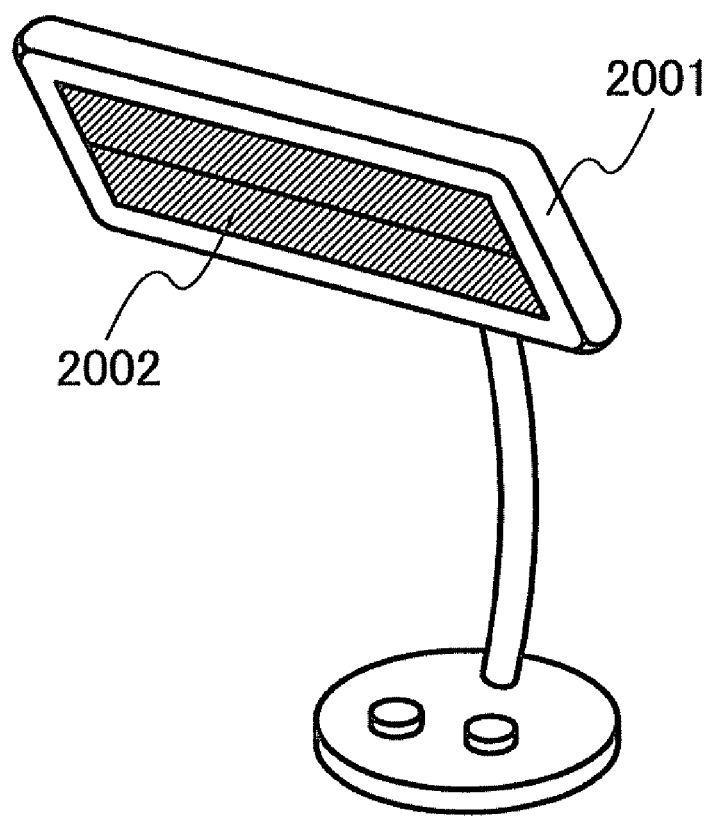
FIG. 12 illustrates a lighting apparatus according to an embodiment of the present invention.

FIG. 12 illustrates an example in which a light-emitting device according to the present invention is used as a desk lamp, which is a lighting apparatus. The desk lamp illustrated in FIG. 12 includes a housing 2001 and a light source 2002, and a light-emitting device according to the present invention is used as the light source 2002. Since power consumption of the light-emitting device of the present invention is reduced, power consumption of the desk lamp with low power consumption is also reduced. Further, since the light-emitting device of the present invention has long lifetime, the desk lamp also has long lifetime.

Figure 13:
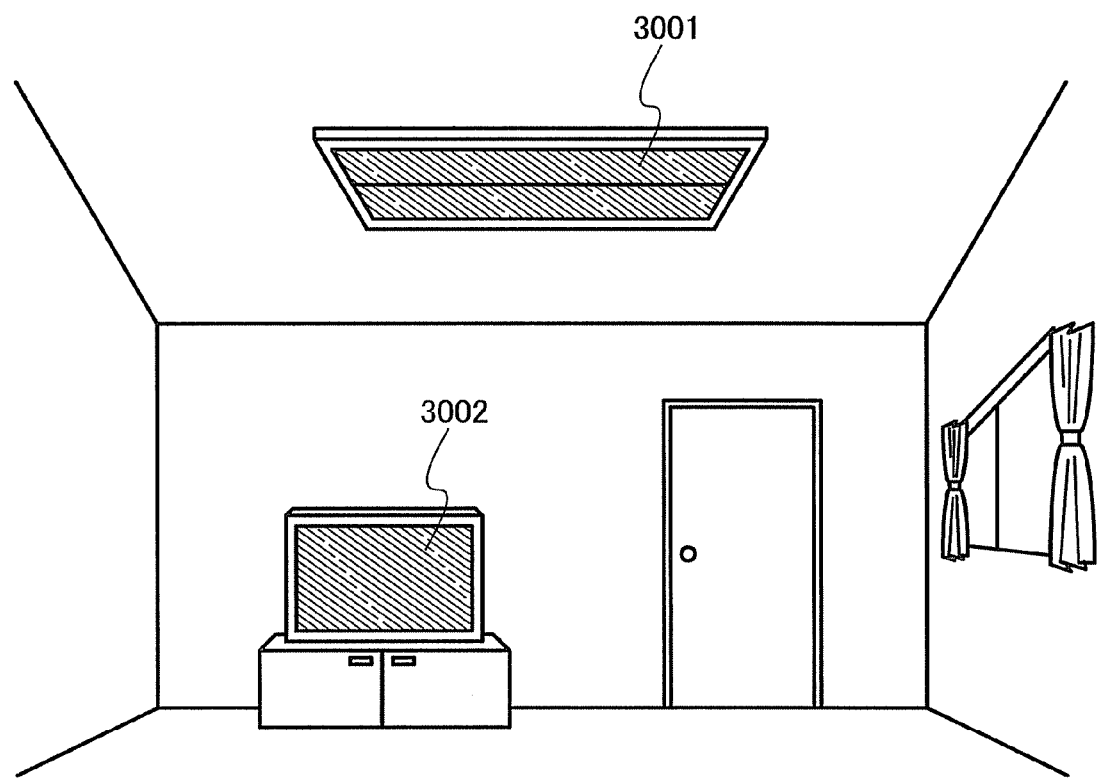
FIG. 13 illustrates a lighting apparatus according to an embodiment of the present invention.

FIG. 13 illustrates an example in which a light-emitting device to which the present invention is applied is used as an interior lighting apparatus 3001. Since the light-emitting device according to the present invention can have a large area, the light-emitting device can be used for a lighting apparatus having a large area. Moreover, since power consumption of the light-emitting device according to the present invention is low, the light-emitting device can be used for a lighting apparatus with low power consumption. In a room where a light-emitting device to which the present invention is thus applied is used for the interior lighting apparatus 3001, a television set 3002 according to the present invention as illustrated in FIG. 8A may be placed, so that public broadcasting or movies can be watched. In such a case, since power consumption of each device is low, environmental load can be reduced. Moreover, since a light-emitting device of the present invention has long lifetime, the light-emitting device can be used for a lighting apparatus having long lifetime. Accordingly, the frequency of replacement of a lighting apparatus or a television set can be reduced, whereby environmental load can be reduced.

Note that Embodiment 6 can be combined with any other embodiment as appropriate.

Example 1

In Example 1, a method of synthesizing 8,11-diphenylacenaphtho[1,2-b]quinoxaline (abbreviation: APzP2) represented by the structural formula (101) is described.

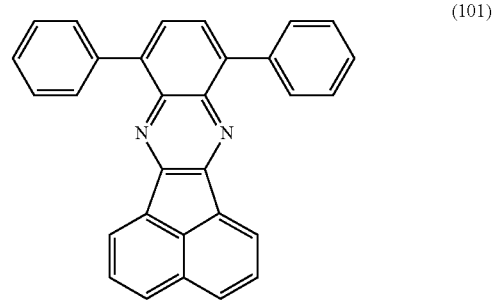

(101)

Step 1: Synthesis of 4,7-Dibromobenzo[2,1,3]thiadiazole

A synthesis scheme of 4,7-dibromobenzo[2,1,3]thiadiazole is illustrated in (B-1).

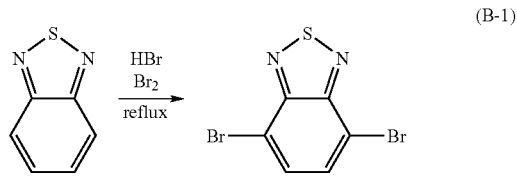

(B-1)

First, in a 500 mL three-necked flask were put 20.0 g (146 mmol) of benzo[2,1,3]thiadiazole and 160 mL of hydrobromic acid (a 48% aqueous solution). While this reaction solution was refluxed at 110° C., 23 mL (446 mmol) of bromine was dropped into the reaction solution. After the completion of the dropping, the mixture was further refluxed at 110° C. for 1 hour. Then, this mixture was washed with water to precipitate a solid, which was collected by suction filtration. The obtained solid was recrystallized with methanol to give 4,7-dibromobenzo[2,1,3]thiadiazole as 31.0 g of a light-brown powdered solid (72% yield).

Step 2: Synthesis of 4,7-Diphenylbenzo[2,1,3]thiadiazole

A synthesis scheme of 4,7-diphenylbenzo[2,1,3]thiadiazole is illustrated in (B-2).

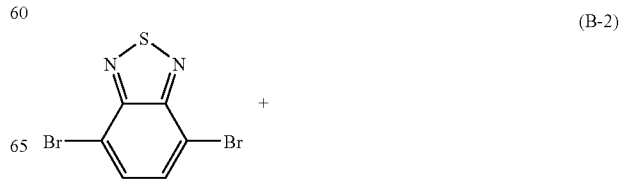

(B-2)

-continued

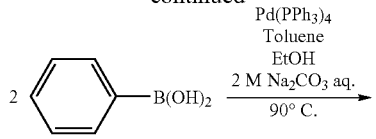

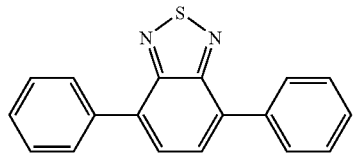

Next, in a 500 mL three-necked flask were put 8.8 g (30 mmol) of 4,7-dibromobenzo[2,1,3]thiadiazole, which was obtained above, 8.3 g (69 mmol) of phenylboronic acid, and 0.69 g (6.0 mmol) of tetrakis(triphenylphosphine)palladium (0). The atmosphere in the flask was replaced with nitrogen. To this mixture were added 100 mL of toluene, 40 mL of ethanol, and 45 mL (90 mmol) of an aqueous sodium carbonate solution (2.0 mol/L). This mixture was stirred under a nitrogen stream at 90° C. for 6 hours. Then, the organic layer of this mixture was washed with water, and the aqueous layer was extracted with ethyl acetate. The extract solution was combined with the organic layer and dried with magnesium sulfate. After being dried, the mixture was suction-filtered, and then the filtrate was concentrated. The obtained residue was dissolved in toluene, and this solution was suction-filtered through Florisil (a product of Wako Pure Chemical Industries, Ltd., Catalog No. 540-00135), Celite (a product of Wako Pure Chemical Industries, Ltd., Catalog No. 531-16855), and alumina. The solid obtained by the concentration of the filtrate was recrystallized with chloroform/hexane to give 4,7-diphenylbenzo[2,1,3]thiadiazole as 8.4 g of a white powdered solid (97% yield).

Step 3: Synthesis of 3,6-Diphenyl-1,2-phenylenediamine

A synthesis scheme of 3,6-diphenyl-1,2-phenylenediamine is illustrated in (B-3).

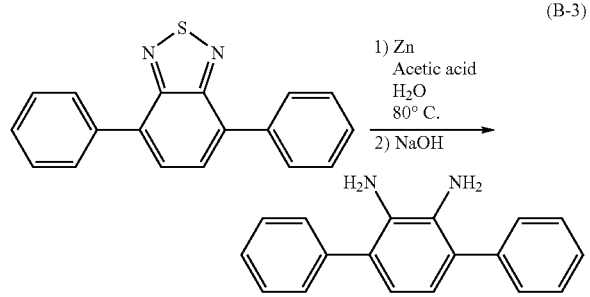

In a 500 mL three-necked flask were put 8.65 g (30.0 mmol) of 4,7-diphenylbenzo[2,1,3]thiadiazole, which was obtained above, 19.6 g (300 mmol) of zinc, 105 mL of glacial acetic acid, and 45 mL of water. This mixture was stirred at 80° C. for 7 hours. After reaction, the reaction solution was poured into about 150 mL of an aqueous sodium hydroxide solution (about 2.0 mol/L), and the mixture was stirred at room temperature for 2 hours. A precipitate in the mixture was collected by suction filtration, and the collected solid was washed with water. The washed solid was dissolved in ethyl acetate. The insoluble material was collected by suction filtration so that zinc was removed. The obtained filtrate was concentrated to give 3,6-diphenyl-1,2-phenylenediamine as 7.6 g of a white powdered solid (96% yield).

Step 4: Synthesis of 8,11-Diphenylacenaphtho[1,2-b]quinoxaline

A synthesis scheme of 8,11-diphenylacenaphtho[1,2-b]quinoxaline is illustrated in (B-4).

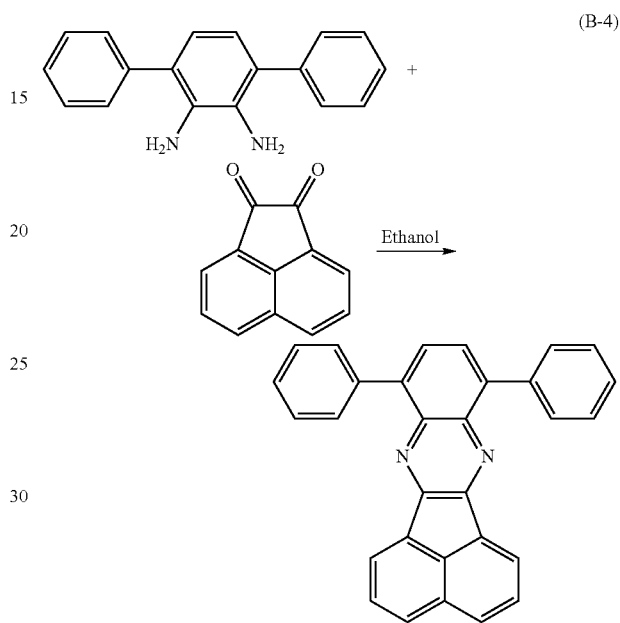

In a 300 L three-necked flask were put 2.7 g (8.7 mmol) of 3,6-diphenyl-1,2-phenylenediamine, which was obtained above, 1.7 g (9.5 mmol) of acenaphthene-1,2-dione, and 60 mL of ethanol. This solution was refluxed for 2.5 hours. After being refluxed, the mixture was cooled to room temperature. Then, by filtration, a milky white solid was collected. The obtained solid was recrystallized with chloroform/ethanol to give the object of the synthesis as 1.9 g at a yield of 52%. Measurement of the obtained solid by the nuclear magnetic resonance (NMR) measurement confirmed that the obtained compound was 8,11-diphenylacenaphtho[1,2-b]quinoxaline (abbreviation: APzP2).

Figure 15A:
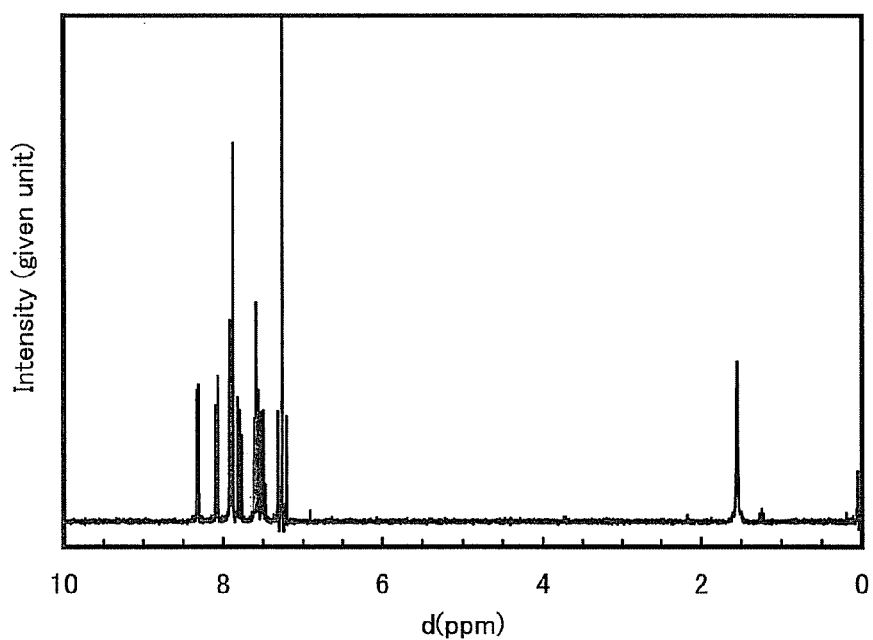
FIGS. 15A and 15B show $^1$H NMR charts of 8,11-diphenylacenaphtho[1,2-b]quinoxaline (abbreviation: APzP2).
Figure 15B:
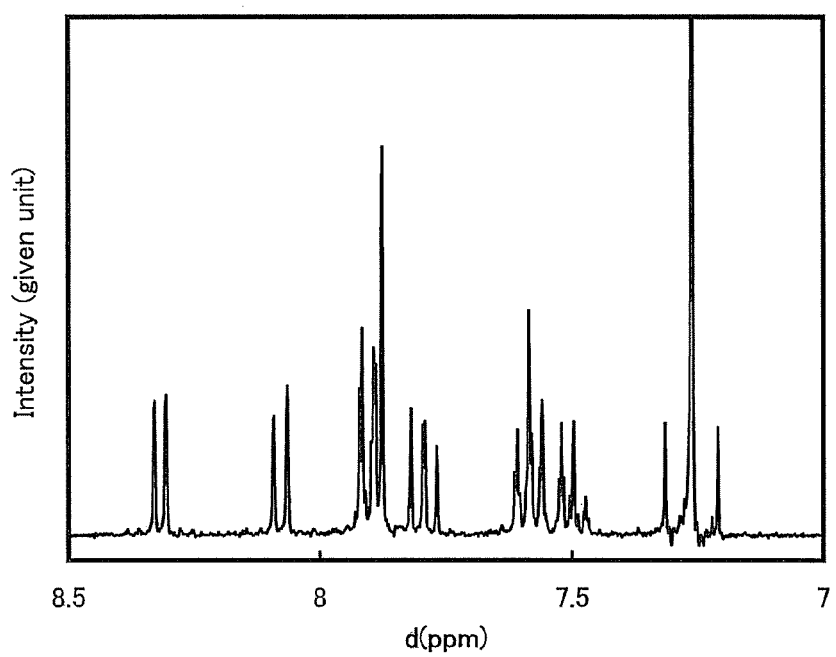

The $^1$H NMR data are shown as follows: $^1$H NMR (CDCl$_3$, 300 MHz): δ=7.47-7.53 (m, 2H), 7.56-7.61 (m, 4H), 7.77-7.82 (m, 2H), 7.88 (s, 2H), 7.91 (d, J1=1.5 Hz, J2=8.4 Hz, 4H), 8.08 (d, J=7.8 Hz, 2H), 8.32 (d, J=6.6 Hz, 2H). Further, FIGS. 15A and 15B show $^1$H NMR charts. Note that FIG. 15B is a chart in which the range of 7.0 to 8.5 ppm in FIG. 15A is enlarged.

Figure 16:
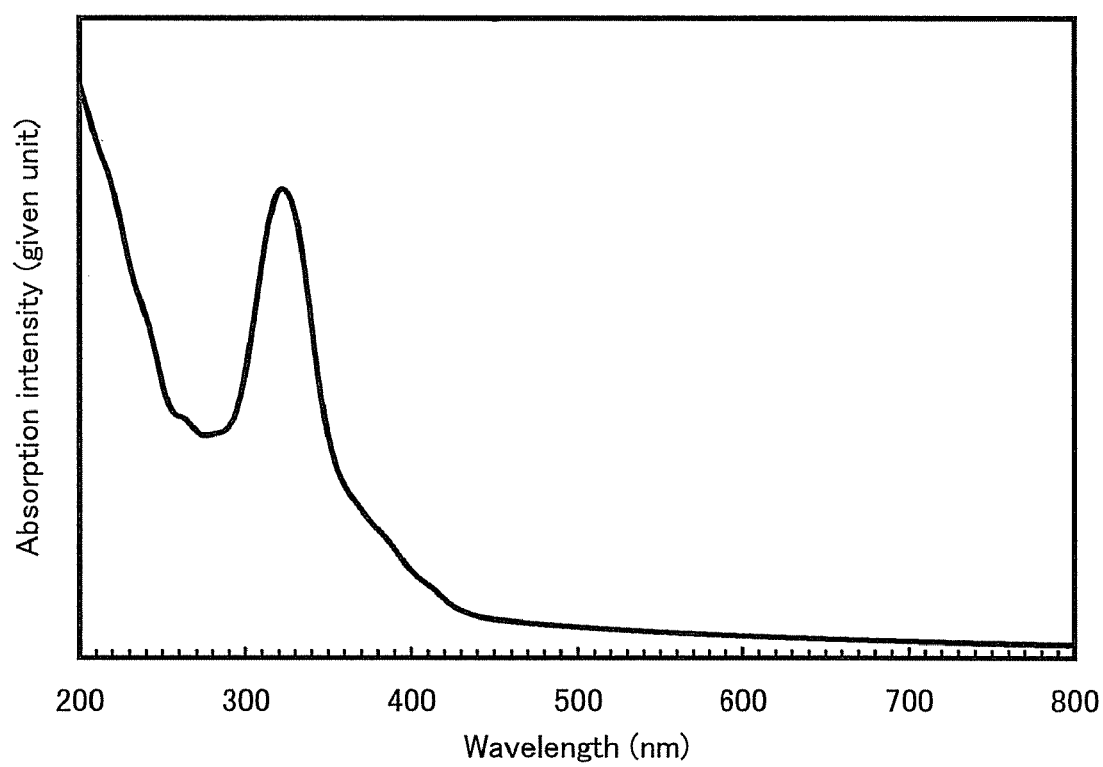
FIG. 16 shows an absorption spectrum of a thin film of 8,11-diphenylacenaphtho[1,2-b]quinoxaline (abbreviation: APzP2).
Figure 17:
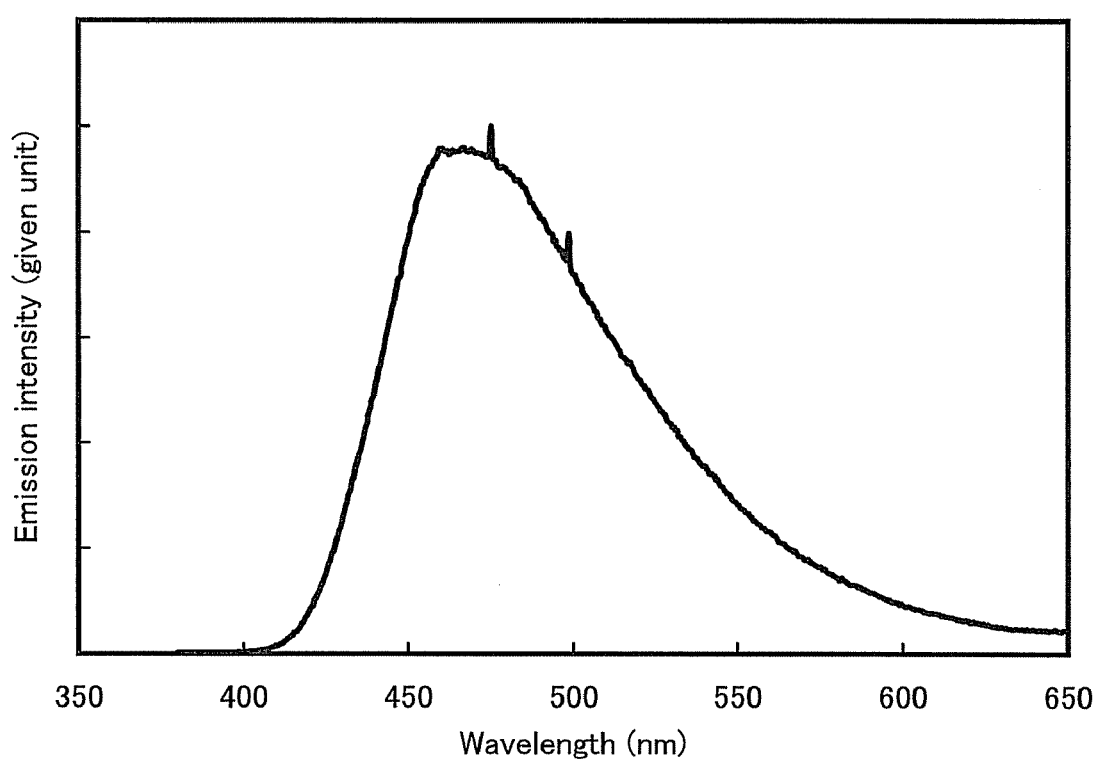
FIG. 17 shows an emission spectrum of the thin film of 8,11-diphenylacenaphtho[1,2-b]quinoxaline (abbreviation: APzP2).

Further, FIG. 16 shows the absorption spectrum of a thin film of APzP2, and FIG. 17 shows the emission spectrum of the thin film of APzP2. An ultraviolet-visible spectrophotometer (V-550, a product of JASCO Corporation) was used for measurement. A sample was prepared on a quartz substrate by an evaporation method, and the absorption spectrum from which the absorption spectrum of quartz is subtracted is shown. In FIG. 16, the horizontal axis represents wavelength (nm) and the vertical axis represents absorption intensity (given unit). Further, In FIG. 17, the horizontal axis represents wavelength (nm) and the vertical axis represents emission intensity (given unit). In the case of the thin film, absorption was observed at around 322 nm. Further, in the case of the thin film, the maximum emission wavelength was 475 nm (excitation wavelength: 322 nm) and blue green light emission was obtained.

Moreover, as a result of measurement with a photoelectron spectrometer (AC-2 photoelectron spectrometer manufactured by Riken Keiki, Co., Ltd.) in the atmosphere, the ionized potential of the thin film of APzP2 was 5.82 eV. Accordingly, it was understood that the HOMO level was −5.82 eV. Furthermore, with the use of the absorption spectrum data of the thin film of APzP2, the absorption edge was obtained by a Tauc plot assuming direct transition. The absorption edge was estimated as an optical energy gap, whereby the energy gap was 2.84 eV. From the obtained values of the energy gap and the HOMO level, the LUMO level was −2.98 eV.

Further, the oxidation-reduction characteristics of APzP2 were measured by cyclic voltammetry (CV). Note that an electrochemical analyzer (ALS model 600A, a product of BAS Inc.) was used for the measurement.

For a solution used in the CV measurement, dehydrated dimethylformamide (DMF, a product of Sigma-Aldrich Inc., 99.8%, Catalog No. 22705-6) was used as a solvent, and tetra-n-butylammonium perchlorate (n-Bu$_4$NClO$_4$, a product of Tokyo Chemical Industry Co., Ltd., Catalog No. T0836), which was a supporting electrolyte, was dissolved in the solvent such that the concentration of tetra-n-butylammonium perchlorate was 100 mmol/L. Furthermore, APzP2, which was the object of the measurement, was dissolved in the solution such that the concentration of APzP2 was 10 mmol/L. A platinum electrode (a product of BAS Inc., PTE platinum electrode) was used as a working electrode, a platinum electrode (a product of BAS Inc., Pt counter electrode for VC-3, (5 cm)) was used as an auxiliary electrode, and an Ag/Ag$^+$ electrode (a product of BAS Inc., RES reference electrode for nonaqueous solvent) was used as a reference electrode. Note that the measurement was conducted at room temperature.

The oxidation characteristics of APzP2 were examined as follows. A scan for changing the potential of the working electrode with respect to the reference electrode from −0.25 V to 1.50 V and then from 1.50 V to −0.25 V was set to one cycle, and the measurement was performed for 100 cycles. Further, the reduction characteristics of APzP2 were examined as follows. A scan for changing the potential of the working electrode with respect to the reference electrode from −0.28 V to −2.30 V and then from −2.30 V to −0.28 V was set to one cycle, and the measurement was performed for 100 cycles. Note that the scan rate for the CV measurement was set to 0.1 V/s.

Figure 18:
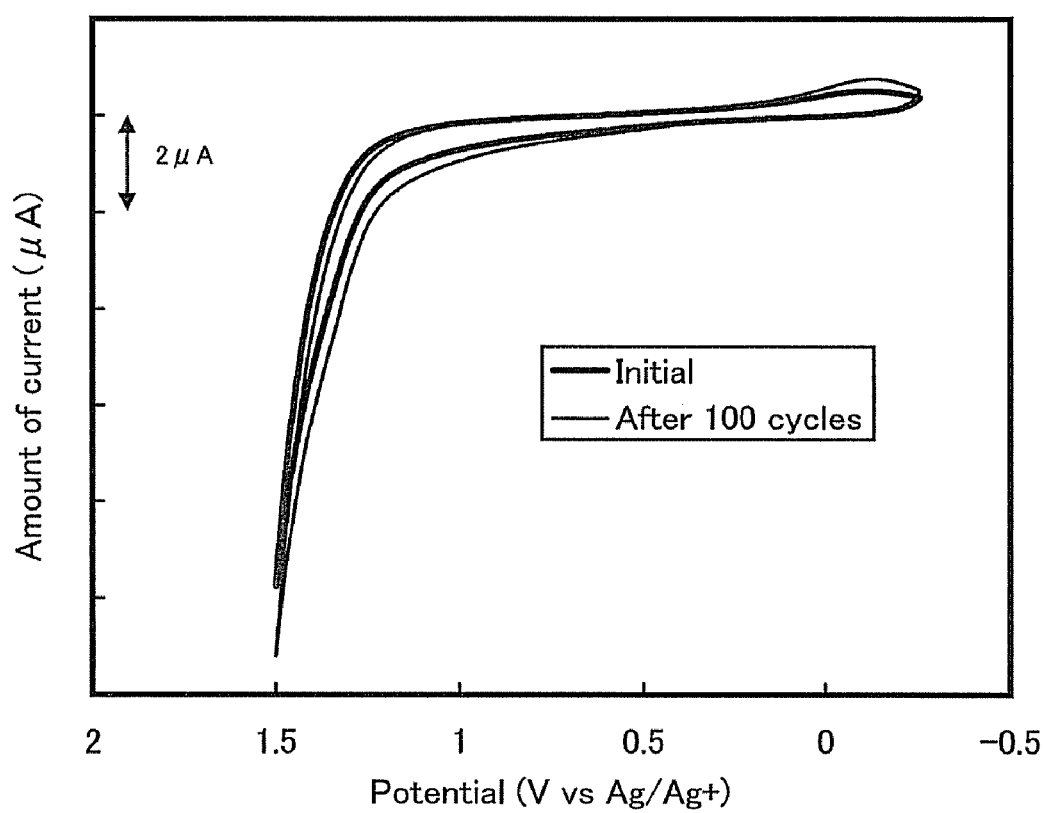
FIG. 18 shows the results of CV measurement of 8,11-diphenylacenaphtho[1,2-b]quinoxaline (abbreviation: APzP2).
Figure 19:
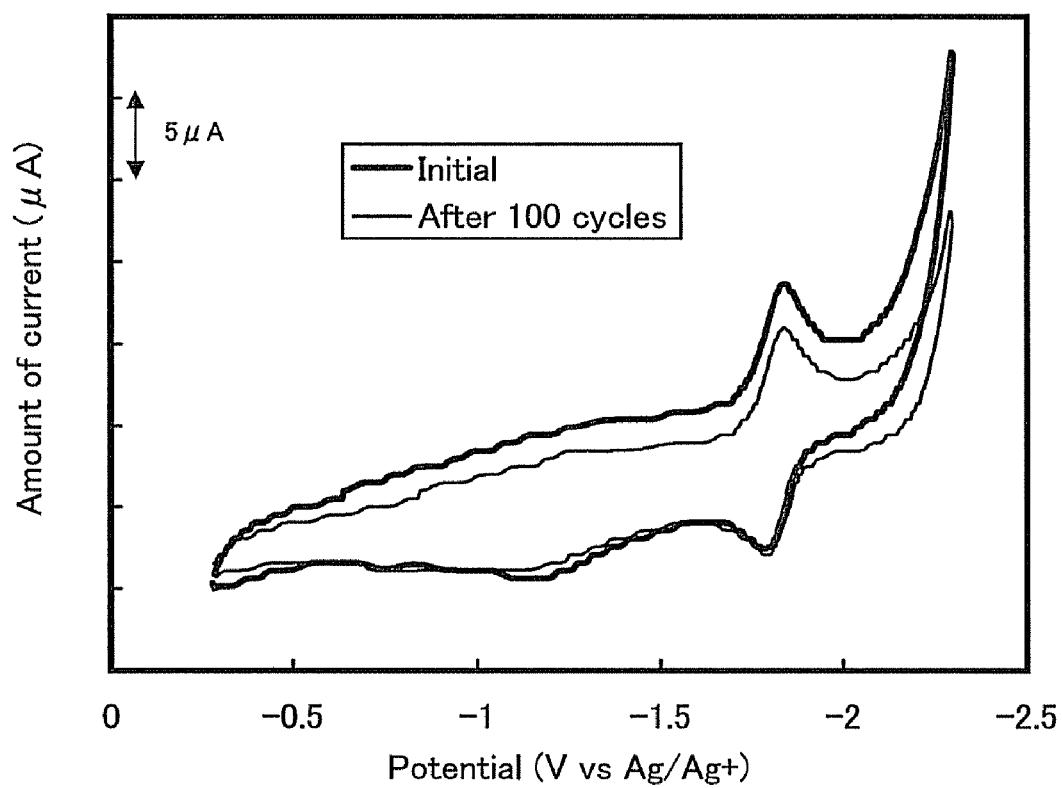
FIG. 19 shows the results of CV measurement of 8,11-diphenylacenaphtho[1,2-b]quinoxaline (abbreviation: APzP2).

FIG. 18 shows CV measurement results of the oxidation characteristics of APzP2. FIG. 19 shows CV measurement results of the reduction characteristics of APzP2. In each of FIG. 18 and FIG. 19, the horizontal axis represents potential (V) of the working electrode with respect to the reference electrode, and the vertical axis represents the amount of current (μA) flowing between the working electrode and the auxiliary electrode. From FIG. 18, although the scan was performed to 1.50 V (vs. the Ag/Ag$^+$ electrode), current exhibiting oxidation was not observed. Further, from FIG. 19, current exhibiting reduction was observed at around −1.84 V (vs. the Ag/Ag$^+$ electrode). Furthermore, although the scan was repeated for as many as 100 cycles, significant changes in the peak position and peak intensity of the CV curves were not observed. This shows that an acenaphthoquinoxaline derivative of the present invention is significantly stable against repetition of reduction reactions. Therefore, an acenaphthoquinoxaline derivative of the present invention can be suitably used for an electronic device such as a light-emitting element or an organic transistor.

Example 2

Figure 20:
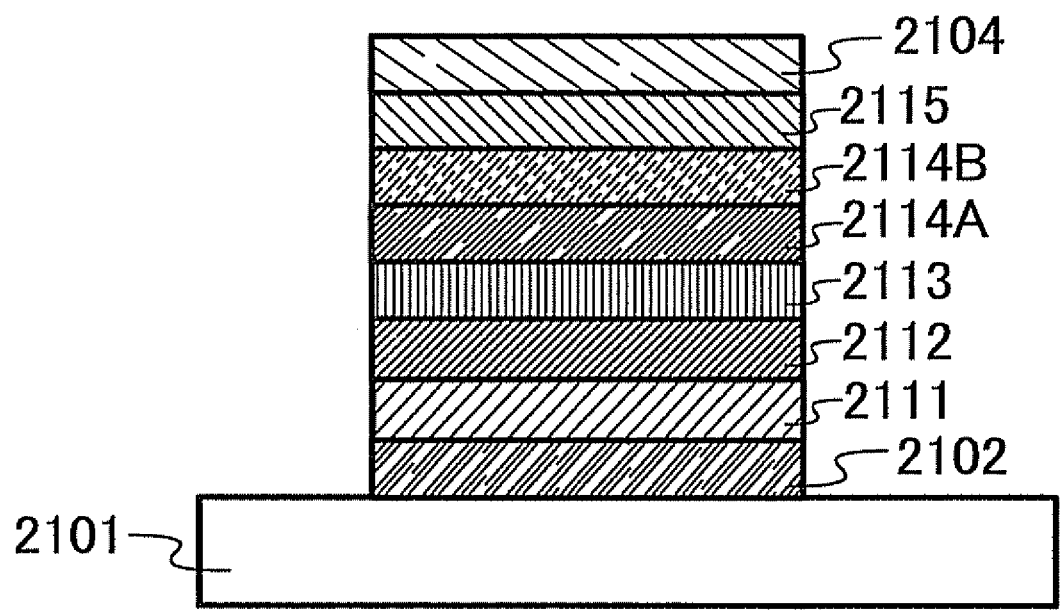
FIG. 20 illustrates a light-emitting element of Example 2.

In Example 2, one example of a light-emitting element of the present invention is described using FIG. 20. Structural formulae of materials used in Example 2 are illustrated below.

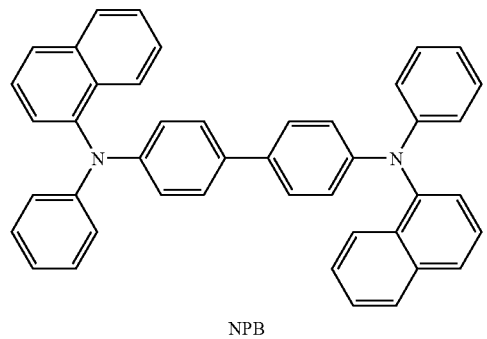

NPB

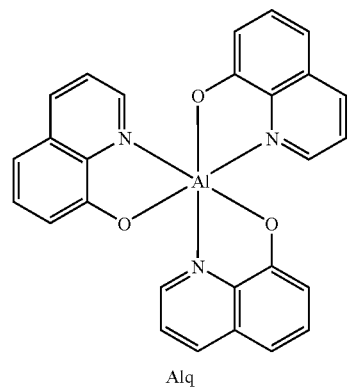

Alq coumarin 6

APzP2

-continued

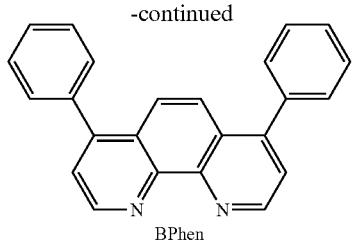
BPhen

Hereinafter, a method of fabricating a light-emitting element of Example 2 is described.

(Light-Emitting Element 1)

First, a film of indium tin oxide containing silicon oxide (ITSO) was formed over a glass substrate 2101 by a sputtering method, whereby a first electrode 2102 was formed. Note that the thickness of the first electrode 2102 was set to 110 nm and the area of the electrode was set to 2 mm×2 mm.

Next, the substrate provided with the first electrode 2102 was fixed to a substrate holder provided in a vacuum evaporation apparatus such that the side on which the first electrode 2102 was formed faced downward. After the pressure was reduced to approximately $10^{-4}$ Pa, 4,4'-bis[N-(1-naphthyl)-N-phenylamino]biphenyl (abbreviation: NPB) and molybdenum(VI) oxide were co-evaporated over the first electrode 2102, whereby a layer 2111 including a composite material of an organic compound and an inorganic compound was formed. The thickness of the layer 2111 was set to 50 nm and the weight ratio of NPB to molybdenum(VI) oxide was adjusted so as to be 4:1 (=NPB:molybdenum oxide). Note that a co-evaporation method refers to an evaporation method by which evaporation is concurrently conducted from a plurality of evaporation sources in one treatment chamber.

Next, a 10-nm-thick film of 4,4'-bis[N-(1-naphthyl)-N-phenylamino]biphenyl (abbreviation: NPB) was formed over the layer 2111 including a composite material by an evaporation method with resistance heating, whereby a hole-transporting layer 2112 was formed.

Furthermore, tris(8-quinolinolato)aluminum(III) (abbreviation: Alq) and coumarin 6 were co-evaporated, whereby a 40-nm-thick light-emitting layer 2113 was formed over the hole-transporting layer 2112. Here, the weight ratio of Alq to coumarin 6 was adjusted to be 1:0.01 (=Alq:coumarin 6).

Then, a 10-nm-thick film of 8,11-diphenylacenaphtho[1,2-b]quinoxaline (abbreviation: APzP2) represented by the structural formula (101) was formed over the light-emitting layer 2113 by an evaporation method with resistance heating, whereby a first electron-transporting layer 2114A was formed. Furthermore, a 20-nm-thick bathophenanthroline (abbreviation: BPhen) film was formed over the first electron-transporting layer 2114A, whereby a second electron-transporting layer 2114B was formed.

Furthermore, a 1-nm-thick lithium fluoride film was formed over the second electron-transporting layer 2114B, whereby an electron-injecting layer 2115 was formed.

Lastly, a 200-nm-thick aluminum film was formed over the electron-injecting layer 2115 by an evaporation method with resistance heating, whereby a second electrode 2104 was formed. Thus, a light-emitting element 1 was fabricated.

The thus obtained light-emitting element 1 was sealed in a glove box containing a nitrogen atmosphere so as not to be exposed to air. Then, operation characteristics of this light-emitting element were measured. Note that the measurement was carried out at room temperature (in the atmosphere kept at 25° C.).

Figure 21:
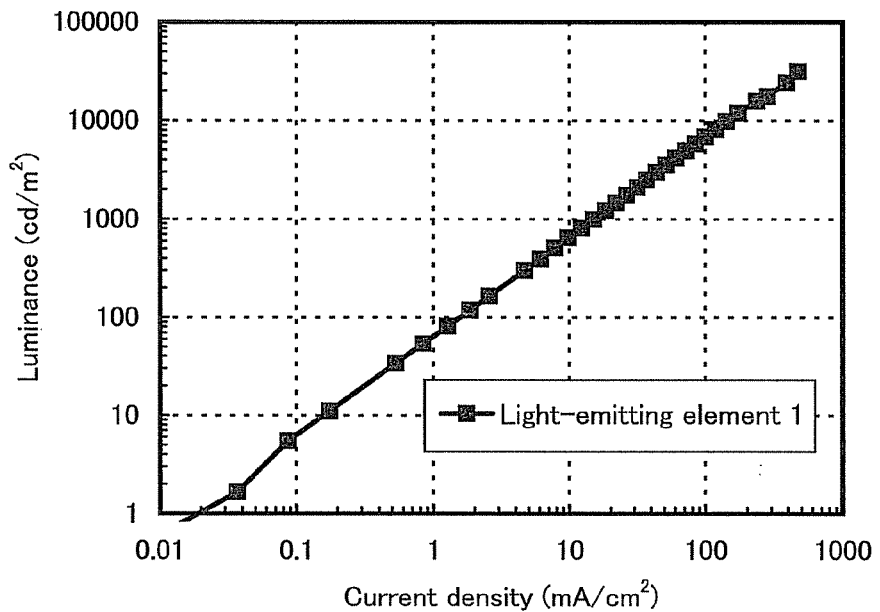
FIG. 21 shows the current density vs. luminance characteristic of a light-emitting element fabricated in Example 2.
Figure 22:
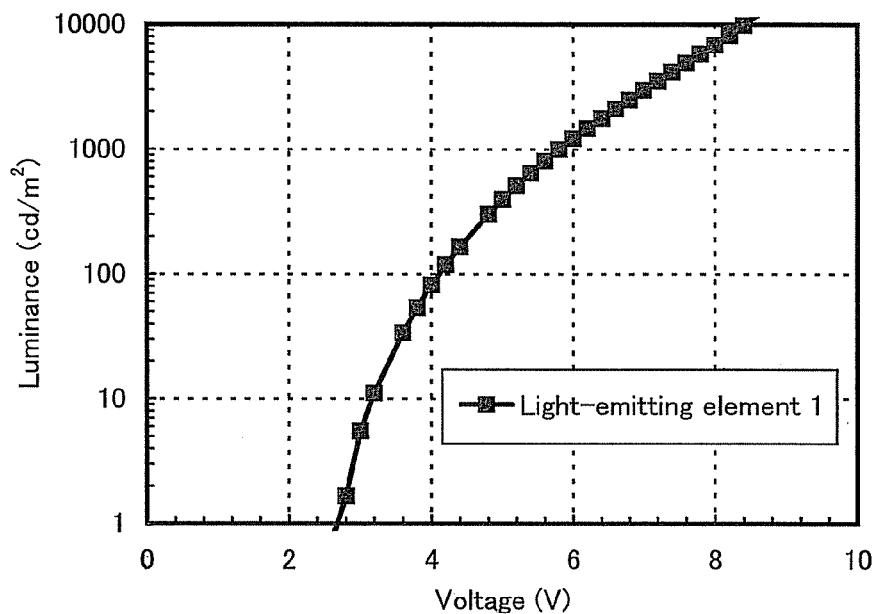
FIG. 22 shows the voltage vs. luminance characteristic of the light-emitting element fabricated in Example 2.
Figure 23:
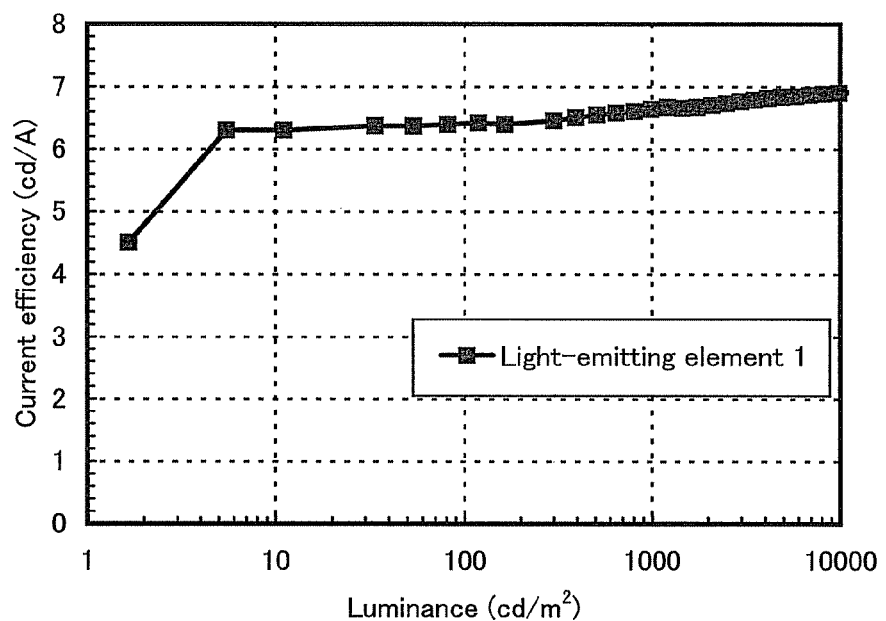
FIG. 23 shows the luminance vs. current efficiency characteristic of the light-emitting element fabricated in Example 2.
Figure 24:
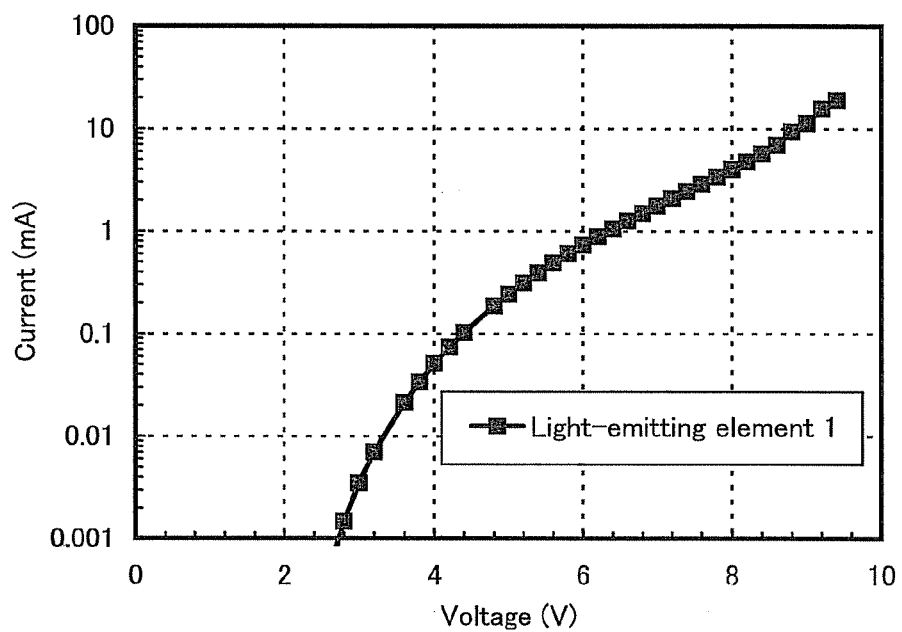
FIG. 24 shows the voltage vs. current characteristic of the light-emitting element fabricated in Example 2.

FIG. 21 shows the current density vs. luminance characteristic of the light-emitting element 1. FIG. 22 shows the voltage vs. luminance characteristic of the light-emitting element 1. FIG. 23 shows the luminance vs. current efficiency characteristic of the light-emitting element 1. FIG. 24 shows the voltage vs. current characteristic of the light-emitting element 1.

Figure 25:
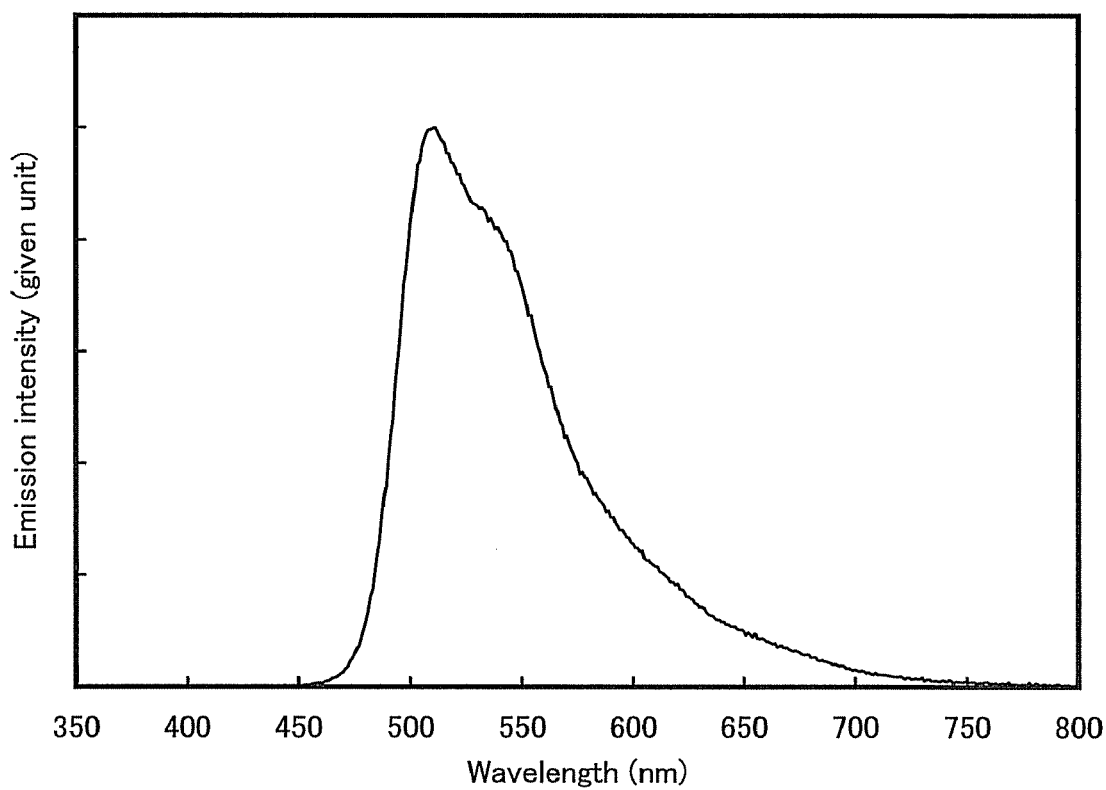
FIG. 25 shows an emission spectrum of the light-emitting element fabricated in Example 2.

Further, FIG. 25 shows the emission spectrum at a current of 1 mA. From FIG. 25, as light emission from the light-emitting element 1, the emission spectrum due to coumarin 6 was obtained.

The CIE chromaticity coordinates of the light-emitting element 1 at a luminance of 1000 cd/m$^2$ were (x=0.30, y=0.62), and green light emission was exhibited. Further, at a luminance of 1000 cd/m$^2$, the current efficiency of the light-emitting element 1 was 6.6 cd/A. Furthermore, at a luminance of 1000 cd/m$^2$, the voltage, current density, and power efficiency of the light-emitting element 1 were 5.8 V, 15.0 mA/cm$^2$, and 3.6 lm/W, respectively.

Thus, the driving voltage and power consumption of the light-emitting element 1 are low. Therefore, by using an acenaphthoquinoxaline derivative of the present invention, the driving voltage and power consumption of a light-emitting element can be reduced.

Example 3

Figure 26:
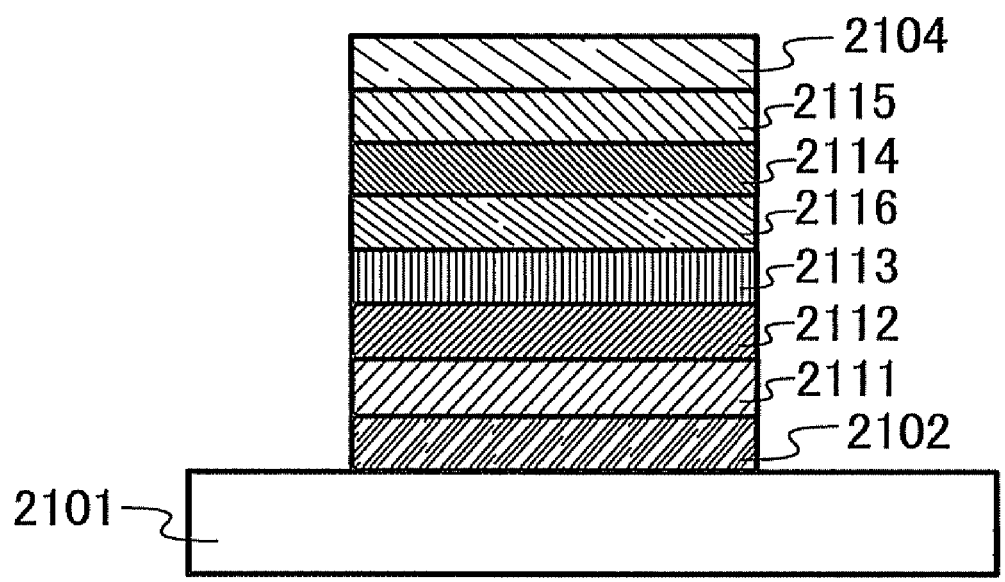
FIG. 26 illustrates a light-emitting element of Example 3.

In Example 3, one example of a light-emitting element of the present invention is described using FIG. 26. Structural formulae of materials used in Example 3 are illustrated below. Note that description of the structural formulae of the materials which have already been illustrated is omitted.

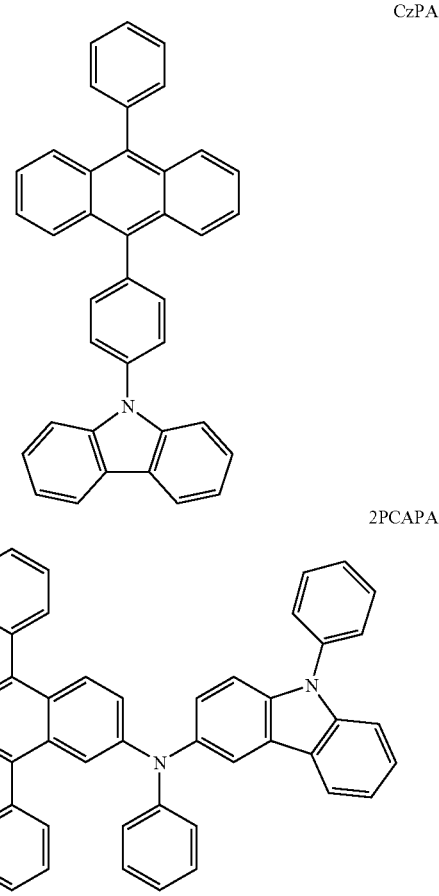

CzPA

2PCAPA

Hereinafter, a method of fabricating a light-emitting element of Example 3 is described.

(Light-Emitting Element 2)

First, a film of indium tin oxide containing silicon oxide (ITSO) was formed over the glass substrate 2101 by a sputtering method, whereby the first electrode 2102 was formed. Note that the thickness of the first electrode 2102 was set to 110 nm and the area of the electrode was set to 2 mm×2 mm.

Next, the substrate provided with the first electrode 2102 was fixed to a substrate holder provided in a vacuum evaporation apparatus such that the side on which the first electrode 2102 was formed faced downward. After the pressure was reduced to approximately $10^{-4}$ Pa, 4,4'-bis[N-(1-naphthyl)-N-phenylamino]biphenyl (abbreviation: NPB) and molybdenum(VI) oxide were co-evaporated over the first electrode 2102, whereby the layer 2111 including a composite material of an organic compound and an inorganic compound was formed. The thickness of the layer 2111 was set to 50 nm and the weight ratio of NPB to molybdenum(VI) oxide was adjusted so as to be 4:1 (=NPB:molybdenum oxide).

Next, a 10-nm-thick film of 4,4'-bis[N-(1-naphthyl)-N-phenylamino]biphenyl (abbreviation: NPB) was formed over the layer 2111 including a composite material by an evaporation method with resistance heating, whereby the hole-transporting layer 2112 was formed.

Furthermore, 9-[4-(10-phenyl-9-anthryl)phenyl]-9H-carbazole (abbreviation: CzPA) and N-(9,10-diphenyl-2-anthryl)-N,9-diphenyl-9H-carbazol-3-amine (abbreviation: 2PCAPA) were co-evaporated, whereby the 30-nm-thick light-emitting layer 2113 was formed over the hole-transporting layer 2112. Here, the weight ratio of CzPA to 2PCAPA was adjusted to be 1:0.05 (=CzPA:2PCAPA).

Then, tris(8-quinolinolato)aluminum(III) (abbreviation: Alq) and 8,11-diphenylacenaphtho[1,2-b]quinoxaline (abbreviation: APzP2) represented by the structural formula (101) were co-evaporated over the light-emitting layer 2113 by an evaporation method with resistance heating, whereby a 10-nm-thick layer 2116 for controlling transport of electrons was formed. Here, the weight ratio of Alq to APzP2 was adjusted to be 1:0.05 (=Alq:APzP2).

Then, a 30-nm-thick bathophenanthroline (abbreviation: BPhen) film was formed over the layer 2116 for controlling transport of electrons by an evaporation method with resistance heating, whereby an electron-transporting layer 2114 was formed.

Furthermore, a 1-nm-thick lithium fluoride film was formed over the electron-transporting layer 2114, whereby the electron-injecting layer 2115 was formed. Lastly, a 200-nm-thick aluminum film was formed over the electron-injecting layer 2115 by an evaporation method with resistance heating, whereby a second electrode 2104 was formed. Thus, a light-emitting element 2 was fabricated.

(Light-Emitting Element 3)

The same kind of substrate as the light-emitting element 2 was used and the weight ratio of Alq to APzP2 in the layer 2116 for controlling transport of electrons was adjusted to be 1:0.10 (=Alq:APzP2), so that a light-emitting element 3 was fabricated. The light-emitting element 3 was fabricated in a manner similar to that of the light-emitting element 2 except for the layer 2116 for controlling transport of electrons.

The thus obtained light-emitting elements 2 and 3 were sealed in a glove box containing a nitrogen atmosphere so as not to be exposed to air. Then, operation characteristics of these light-emitting elements were measured. Note that the measurement was carried out at room temperature (in the atmosphere kept at 25° C.).

Figure 27:
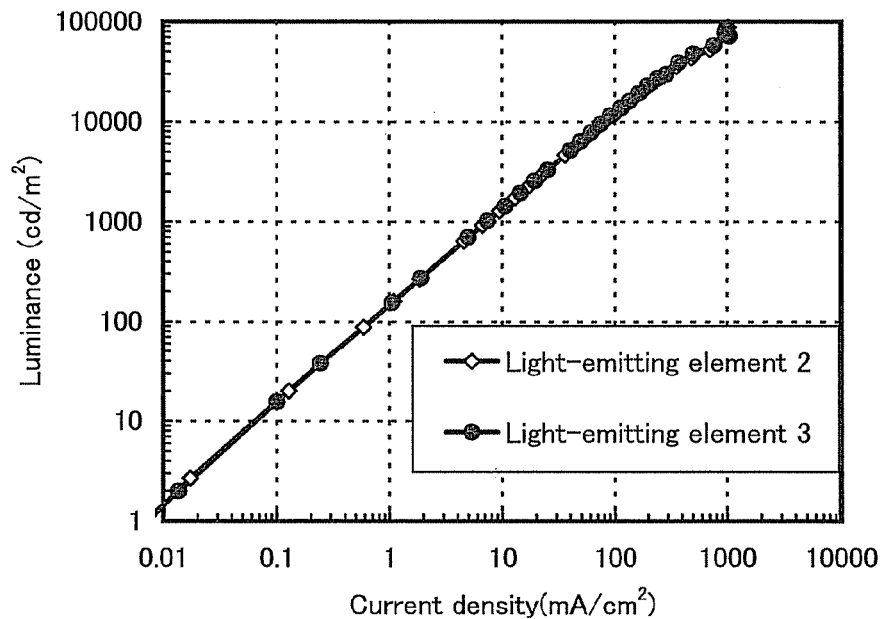
FIG. 27 shows the current density vs. luminance characteristics of light-emitting elements fabricated in Example 3.
Figure 28:
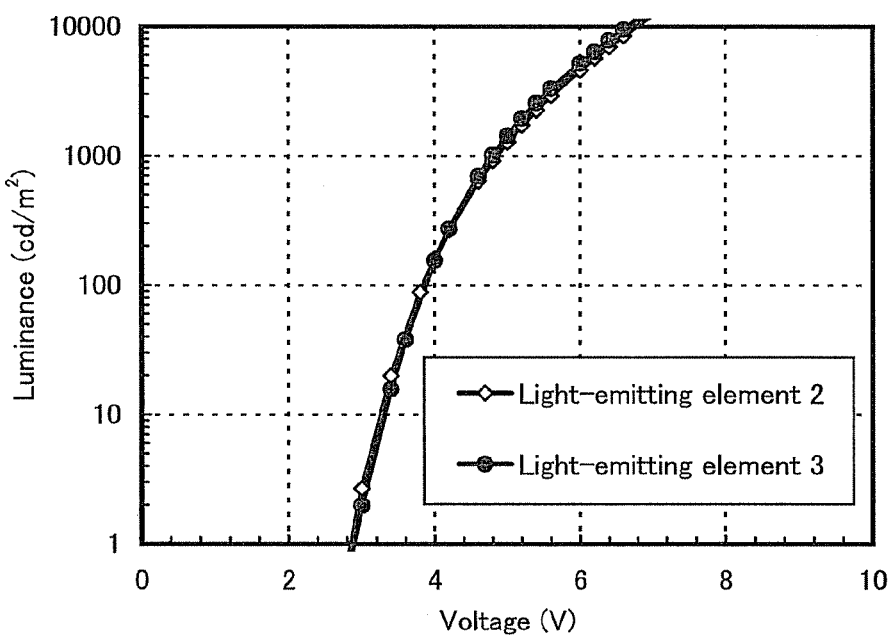
FIG. 28 shows the voltage vs. luminance characteristics of the light-emitting elements fabricated in Example 3.
Figure 29:
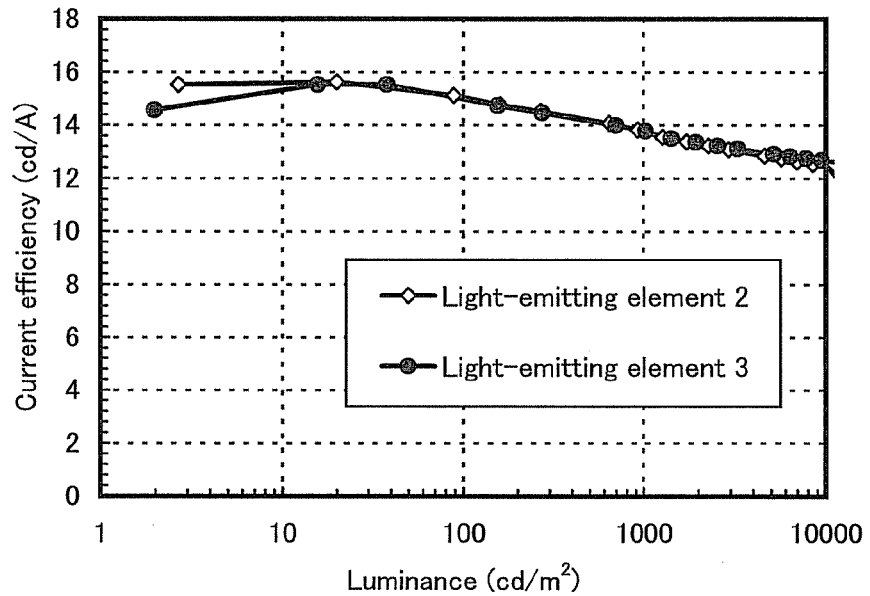
FIG. 29 shows the luminance vs. current efficiency characteristics of the light-emitting elements fabricated in Example 3.
Figure 30:
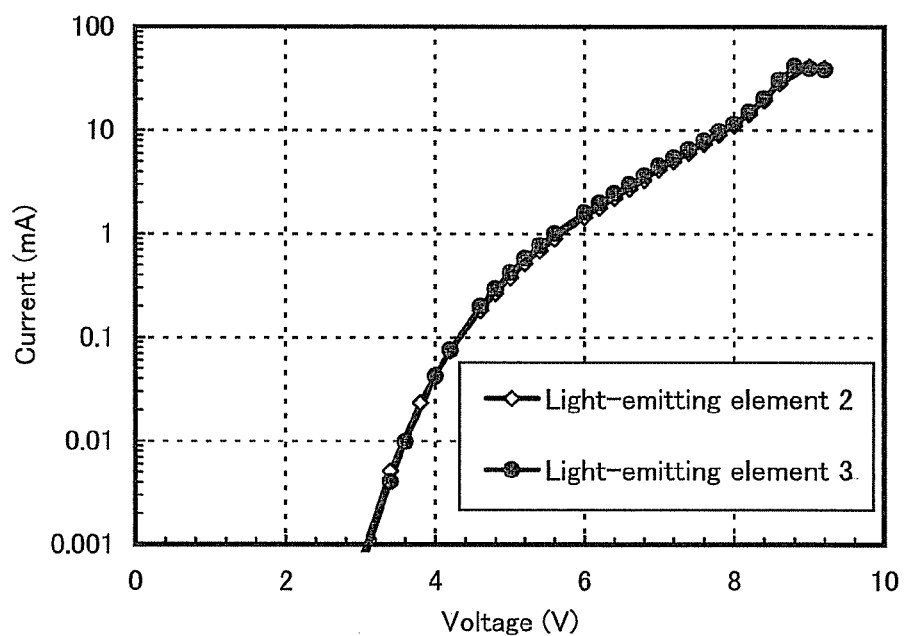
FIG. 30 shows the voltage vs. current characteristics of the light-emitting elements fabricated in Example 3.

FIG. 27 shows the current density vs. luminance characteristics of the light-emitting elements 2 and 3 FIG. 28 shows the voltage vs. luminance characteristics of the light-emitting elements 2 and 3. FIG. 29 shows the luminance vs. current efficiency characteristics of the light-emitting elements 2 and 3. FIG. 30 shows the voltage vs. current characteristics of the light-emitting elements 2 and 3.

Figure 31:
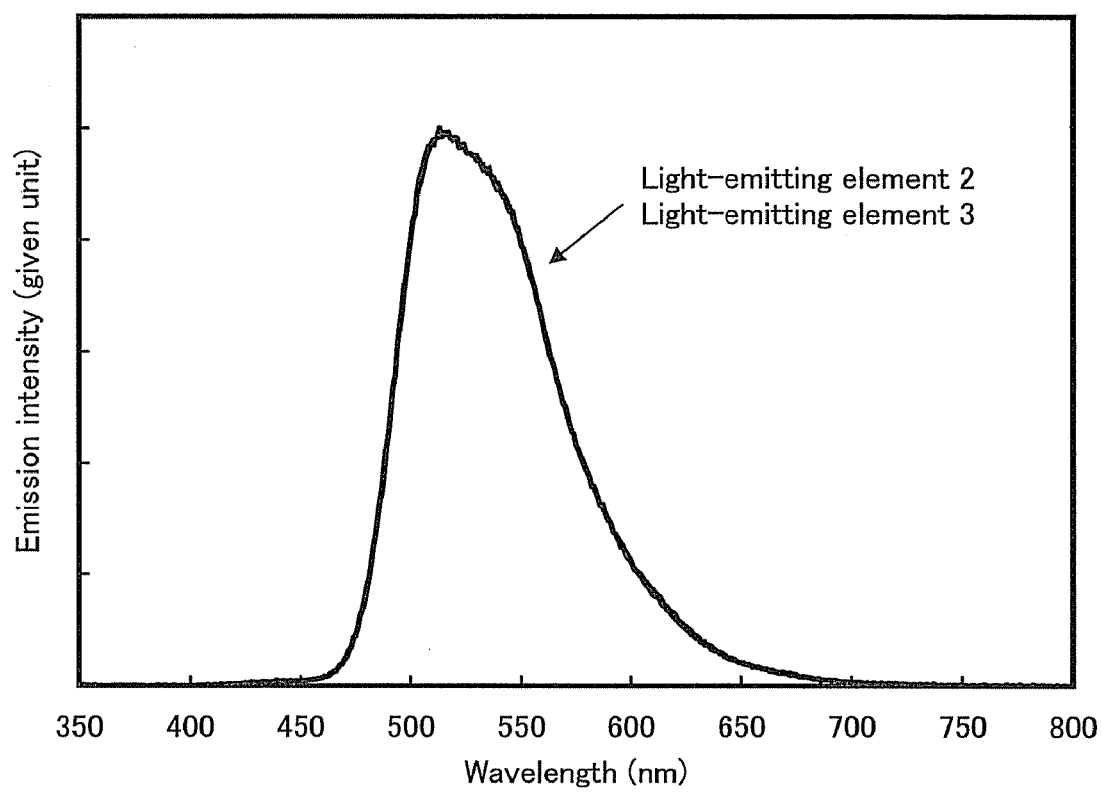
FIG. 31 shows an emission spectrum of the light-emitting elements fabricated in Example 3.

Further, FIG. 31 shows the emission spectra at a current of 1 mA. FIG. 31 indicates that the emission spectra of the light-emitting element 2 and the light-emitting element 3 are the same or substantially the same and that light emission due to 2PCAPA was obtained.

The CIE chromaticity coordinates of the light-emitting element 2 at a luminance of 2920 cd/m$^2$ were (x=0.29, y=0.62), and green light emission was exhibited. Further, at a luminance of 2920 cd/m$^2$, the current efficiency of the light-emitting element 2 was 13.1 cd/A. Furthermore, at a luminance of 2920 cd/m$^2$, the voltage, current density, and power efficiency of the light-emitting element 2 were 5.6 V: 22.3 mA/cm$^2$, and 7.3 lm/W, respectively.

The CIE chromaticity coordinates of the light-emitting element 3 at a luminance of 3290 cd/m$^2$ were (x, y)=(0.29, 0.62), and green light emission was exhibited. Further, at a luminance of 3290 cd/m$^2$, the current efficiency of the light-emitting element 3 was 13.1 cd/A. Furthermore, at a luminance of 3290 cd/m$^2$, the voltage, current density, and power efficiency of the light-emitting element 3 were 5.6 V, 25.1 mA/cm$^2$, and 7.4 lm/W, respectively.

Figure 32:
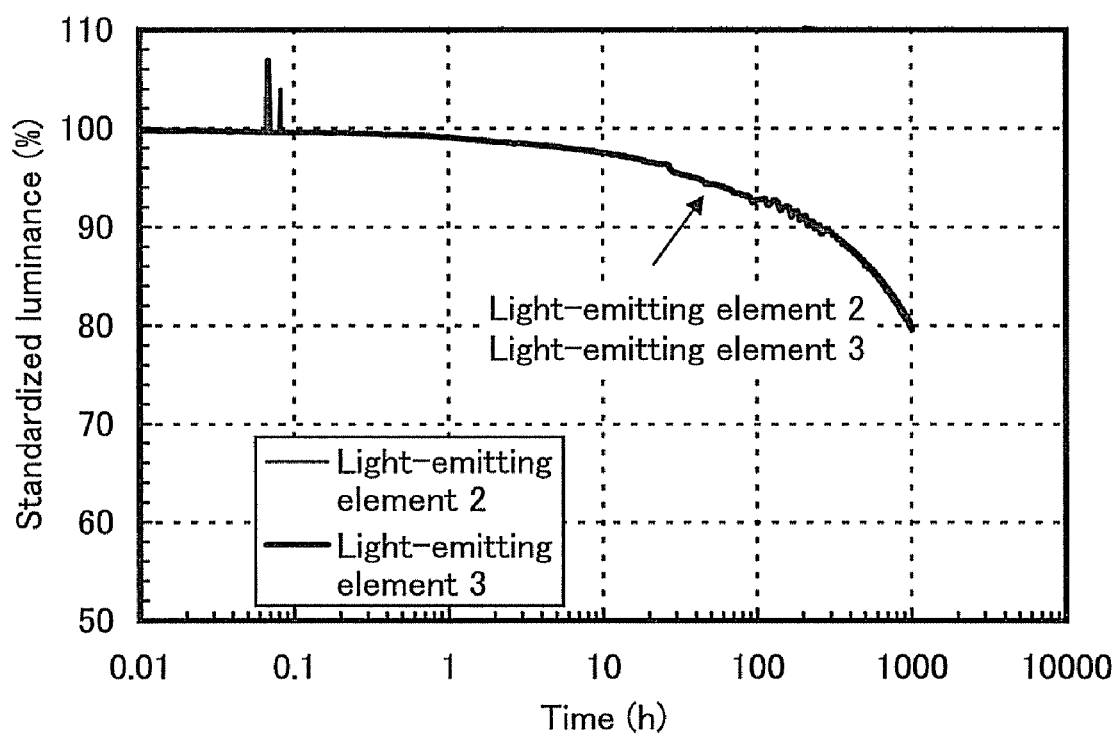
FIG. 32 shows changes in the luminance of the light-emitting elements fabricated in Example 3 with respect to driving time.

Further, FIG. 32 shows the results of continuous lighting tests in which the light-emitting elements 2 and 3 were continuously lit by constant current driving with the initial luminance thereof set to 5000 cd/m$^2$ (the vertical axis represents relative luminance on condition that 5000 cd/m$^2$ was 100%). As can be seen from FIG. 32, the light-emitting elements 2 and 3 each kept 80% of the initial luminance even after 1000 hours and found to have long lifetime.

Therefore, since an acenaphthoquinoxaline derivative of the present invention easily receives electrons, by using the derivative for a layer for controlling transport of electrons, a light-emitting element having long lifetime can be obtained.

The present application is based on Japanese Patent Application serial No. 2008-087308 filed with Japan Patent Office on Mar. 28, 2008, the entire contents of which are hereby incorporated by reference.

What is claimed is:

1. An acenaphthoquinoxaline derivative represented by a general formula (G1),

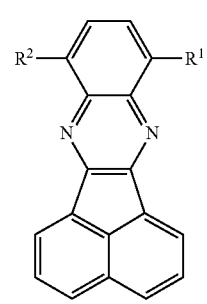

(G1)

wherein R$^1$ represents a substituted or unsubstituted aryl group having 6 to 13 carbon atoms, and R$^2$ represents a substituted or unsubstituted aryl group having 6 to 13 carbon atoms.

2. The acenaphthoquinoxaline derivative according to claim 1, wherein R$^1$ represents a substituted or unsubstituted phenyl group and R$^2$ represents a substituted or unsubstituted phenyl group.

3. The acenaphthoquinoxaline derivative according to claim 1 is represented by a structural formula (101)

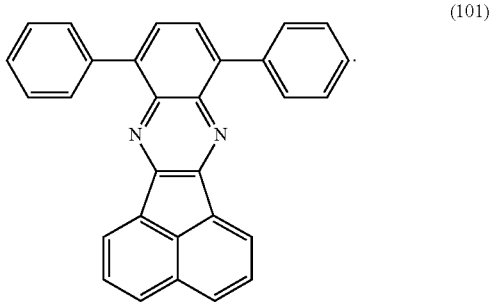
(101)

4. A light-emitting device comprising a layer including an acenaphthoquinoxaline derivative,
wherein the acenaphthoquinoxaline derivative is represented by a general formula (G1),

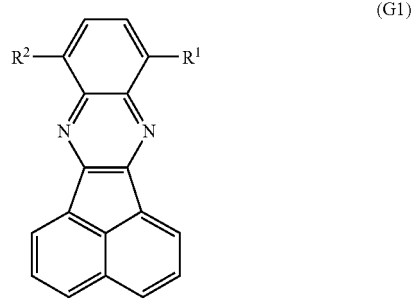
(G1)

wherein $R^1$ represents a substituted or unsubstituted aryl group having 6 to 13 carbon atoms, and $R^2$ represents a substituted or unsubstituted aryl group having 6 to 13 carbon atoms.

5. The light-emitting device according to claim 4, wherein $R^1$ represents a substituted or unsubstituted phenyl group and $R^2$ represents a substituted or unsubstituted phenyl group.

6. The light-emitting device according to claim 4, wherein the acenaphthoquinoxaline derivative is represented by a structural formula (101)

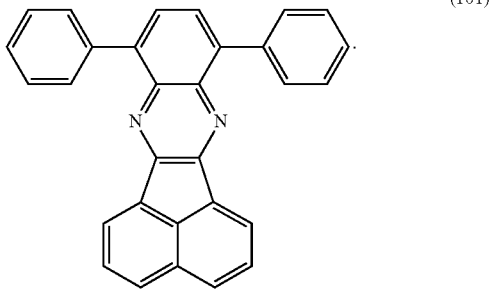
(101)

7. The light-emitting device according to claim 4, further comprising a pair of electrodes wherein the layer including the acenaphthoquinoxaline derivative is provided between the pair of electrodes.

8. The light-emitting device according to claim 4, further comprising a light-emitting layer, an anode and a cathode,
wherein the light-emitting layer and the layer including the acenaphthoquinoxaline derivative are provided between the anode and the cathode, and
wherein the layer including the acenaphthoquinoxaline derivative is provided between the light-emitting layer and the cathode.

9. The light-emitting device according to claim 4,
wherein the layer including the acenaphthoquinoxaline derivative further includes an electron-transporting material,
wherein an amount of the electron-transporting material is larger than an amount of the acenaphthoquinoxaline derivative, and
wherein a lowest unoccupied molecular orbital level of the electron-transporting material is higher than a lowest unoccupied molecular orbital level of the acenaphthoquinoxaline derivative.

10. An electronic device comprising a display portion,
wherein the display portion comprises a layer including an acenaphthoquinoxaline derivative,
wherein the acenaphthoquinoxaline derivative is represented by a general formula (G1),

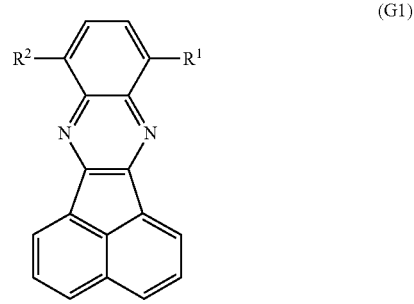
(G1)

wherein $R^1$ represents a substituted or unsubstituted aryl group having 6 to 13 carbon atoms, and $R^2$ represents a substituted or unsubstituted aryl group having 6 to 13 carbon atoms.

11. The electronic device according to claim 10, wherein $R^1$ represents a substituted or unsubstituted phenyl group and $R^2$ represents a substituted or unsubstituted phenyl group.

12. The electronic device according to claim 10, wherein the acenaphthoquinoxaline derivative is represented by a structural formula (101)

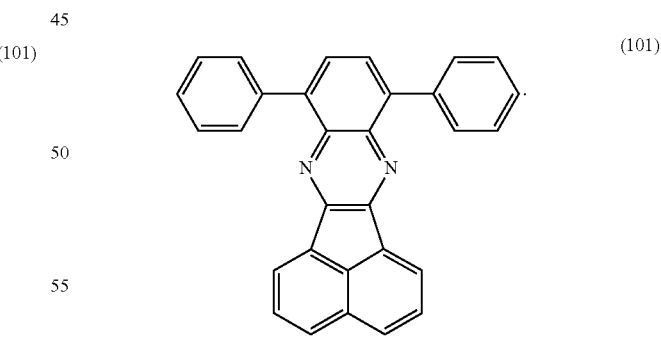
(101)

13. The electronic device according to claim 10, further comprising a pair of electrodes wherein the layer including the acenaphthoquinoxaline derivative is provided between the pair of electrodes.

14. The electronic device according to claim 10, further comprising a light-emitting layer, an anode and a cathode,
wherein the light-emitting layer and the layer including the acenaphthoquinoxaline derivative are provided between the anode and the cathode, and wherein the layer including the acenaphthoquinoxaline derivative is provided between the light-emitting layer and the cathode.

15. The electronic device according to claim 10,
wherein the layer including the acenaphthoquinoxaline derivative further includes an electron-transporting material,
wherein an amount of the electron-transporting material is larger than an amount of the acenaphthoquinoxaline derivative, and
wherein a lowest unoccupied molecular orbital level of the electron-transporting material is higher than a lowest unoccupied molecular orbital level of the acenaphthoquinoxaline derivative.

16. A lighting apparatus comprising the light-emitting device according to claim 4.

* * * * *